US011607422B2

United States Patent
Anto et al.

(10) Patent No.: US 11,607,422 B2
(45) Date of Patent: *Mar. 21, 2023

(54) UTTROSIDE B AND DERIVATIVES THEREOF AS THERAPEUTICS FOR HEPATOCELLULAR CARCINOMA

(71) Applicant: Rajiv Gandhi Centre for Biotechnology, an Autonomous Institute under the Department of Biotechnology, Thiruvananthapuram (IN)

(72) Inventors: Ruby John Anto, Thrissur (IN); Lekshmi Reghu Nath, Thiruvananthapuram (IN)

(73) Assignee: RAJIV GANDHI CENTRE FOR BIOTECHNOLOGY, AN AUTONOMOUS INSTITUTE UNDER THE DEPARTMENT OF BIOTECHNOLOGY. GOVERNMENT OF INDIA, Thiruvananthapuram (IN)

(*) Notice: Subject to any disclaimer, the term of this patent is extended or adjusted under 35 U.S.C. 154(b) by 52 days.

This patent is subject to a terminal disclaimer.

(21) Appl. No.: 17/161,928

(22) Filed: Jan. 29, 2021

(65) Prior Publication Data

US 2021/0154220 A1 May 27, 2021

Related U.S. Application Data

(63) Continuation of application No. 16/304,630, filed as application No. PCT/IN2017/050204 on May 27, 2017.

(30) Foreign Application Priority Data

May 28, 2016 (IN) .............................. 201641018401

(51) Int. Cl.
| A61K 31/7048 | (2006.01) |
| A61K 31/44 | (2006.01) |
| A61K 31/4706 | (2006.01) |
| A61K 47/22 | (2006.01) |

(52) U.S. Cl.
CPC .......... *A61K 31/7048* (2013.01); *A61K 31/44* (2013.01); *A61K 31/4706* (2013.01); *A61K 47/22* (2013.01)

(58) Field of Classification Search
None
See application file for complete search history.

(56) References Cited

U.S. PATENT DOCUMENTS

| 7,078,063 B2 | 7/2006 | Kuo |
| 8,552,161 B2 | 10/2013 | Morzycki et al. |

FOREIGN PATENT DOCUMENTS

| CN | 102652792 A | 9/2012 |
| JP | 2001186879 A | 7/2001 |
| JP | 2002226370 A | 8/2002 |
| JP | 2010215585 A | 9/2010 |
| JP | 2015520206 A | 7/2015 |
| JP | 2016513736 A | 5/2016 |
| WO | 2002005624 | 9/2004 |
| WO | 201708254 A1 | 12/2017 |

OTHER PUBLICATIONS

Jin et al. J. Nat. Prod. (2004), vol. 67, pp. 5-9.*
Yang et al. J. Agric. Food Chem. (2010), vol. 58, pp. 5806-5814.*
Guo et al. Asian Journal of Chemistry (2014), vol. 26, pp. 4615-4618.*
Zhu et al. Clinical Cancer Research (2013), vol. 19, pp. 920-928.*
Shimizu, Satoshi, et al. "Inhibition of autophagy potentiates the antitumor effect of the multikinase inhibitor sorafenib in hepatocellular carcinoma." International journal of cancer 131.3 (2012): 548-557.*
Banerji, Biswadip, et al. "Conformation and cytotoxicity of a tetrapeptide constellated with alternative D-and L-proline." Rsc Advances 2.17 (2012): 6744-6747.*
Locigno, Roberto, and Vincent Castronovo. "Reduced glutathione system: role in cancer development, prevention and treatment." International journal of oncology 19.2 (2001): 221-236.*
Notification of Reasons for Refusal in corresponding Japanese Application No. 2019-514883, dated Aug. 31, 2020 (machine translation).
Lu Rumei et al., The Progress of Research on Solanum nigrum, Lishizhen Medicine and Materia Medica Research, Jul. 20, 2009, pp. 1821-1822.
First Office Action in corresponding Chinese Application No. 201780046877.6, dated Aug. 5, 2020.
Search Report in corresponding Chinese Application No. 201780046877.6, dated Jul. 31, 2020.
Examination Report in corresponding European Application No. 17743096.4, dated Sep. 10, 2020.

(Continued)

*Primary Examiner* — Patrick T Lewis
(74) *Attorney, Agent, or Firm* — Leason Ellis LLP

(57) ABSTRACT

The present invention includes Uttroside B compositions and method for the treatment of hepatocellular carcinoma. Chemotherapeutic options for liver cancer are limited and the prognosis of HCC patients remains dismal. Sorafenib, is the only drug currently available for the treatment of hepatocellular carcinoma.

17 Claims, 19 Drawing Sheets

Specification includes a Sequence Listing.

(56) References Cited

OTHER PUBLICATIONS

Travrso, et al., "Role of Glutathione in Cancer Progression and Chemoresistance," Oxidative Medicine and Cellular Longevity, vol. 2013, 10 pp.
Second Office Action in corresponding Chinese Application No. 201780046877.6, dated Apr. 6, 2021 (an English translation attached hereto).
Luo Wenjuan at al., "The cytotocity of spirostanol saponin on hepatoma cell line," Modem Oncology, Mar. 2007, vol. 15, No. 3, pp. 307-308.
Zhao Xiaoqin et al., "Clinical Study of Longkui Tablets on Treatment of Primary Liver Cancer," Liaoning Journal of Traditional Chinese Medicine, Nov. 2002, vol. 29, No. 11, pp. 671-672.
Re-examined Office Action of corresponding Korean Patent Application No. 10-2018-7036147.
Chinese Office Action in corresponding Chinese Application No. 201780046877.6, dated Sep. 1, 2021 (an English translation attached hereto).
Examination Report in corresponding Indian Application No. 201641018401, dated Jun. 16, 2020.
Notice of Final Rejection in corresponding Korean Patent Application No. 10-2018-7036147, dated Oct. 26, 2020.
PCT/IN2017/050204 International Search Report and Written Opinion of the European Patent Office dated Oct. 26, 2017, 12 pp.
Chen, Xiao-qing, et al., "Microwave-assisted extraction of plysaccarides from solanum nigrum," J. Cent South. Univ. Technol.,vol. 12, No. 5, Oct. 2005, pp. 556-560.
Guo, Shan-Bin, et al., "Optimization of Ethanol Extraction Process of Solanum nigrum Linn., and Structural Confirmation of its Compounds," Asian Journal of Chemistry, vol. 26, No. 15, Jul. 16, 2014, pp. 4615-4618.
Jin, Jian-Ming, et al., "Spirostanol and Furostanol Glycosides from the Fresh Tubers of *Polianthes tuberosa*," J. Nat. Prod., vol. 67, 2004 (published Dec. 12, 2003) pp. 5-9.
Lin, Hui-Mei, et al., "Hepatoprotective effects of Solanum nigrum Linn extract against CC14-iduced oxidative damage in rats," Chemico-Biological Interactions, vol. 171, Aug. 19, 2007, pp. 283-293.
Lin, Hui-Mei, et al., "Induction of Autophagy and Apoptosis by the Extract of Solanum nigrum Linn in HepG2 Cells", Journal of Agricultural and Food Chemistry, vol. 55, Apr. 10, 2007, pp. 3620-3628.
Nath, Lekshmi, et al., "Evaluation of uttroside B, a saponin from Solanum nigrum Linn, as a promising chemotherapeutic agent against hepatocellular carcinoma," Scientific Reports, Nov. 3, 2016, pp. 1-13.
Sharma, S.C., et al., "Oligofurostanosides from Solanum Nigrum," Phytochemistry, vol. 22, No. 5, Sep. 13, 1982, pp. 1241-1244.
Wang, Hsueh-Chun, et al., "*Solanum nigrum* L. Polyphenolic extract inhibits hepatocarcinoma cell growth by inducing G2/M phase arrest and apoptosis," J. Sci. Food Agric., vol. 91, Sep. 17, 2010, pp. 178-185.
Yang, Mon-Yuan, et al., "Polyphenol-Rich Extracts from Solanum nigrum Attenuated PKG a-Mediated Migration and Invasion of Hepatocellular Carcinoma Cells, "J. Agric. Food Chem., vol. 58, Mar. 29, 2010, pp. 5806-5814.
Amin, et al. "Perspectives for Cancer Prevention With Natural Compounds" J. Clin. Oncol. Jun. 1, 2009, 27, 2712-2725.
Antony, et al. "DW-F5: A novel formulation against malignant melanoma from Wrightia tinctoria" J. Sci. Rep. 2015, 5, (received:Jan. 11, 2015) 11107.
Da Rocha, et al. "Natural products in anticancer therapy" Curr. Opin. Pharmacol. 2001, 1, 364-369.
Franken, et al. Clonogenic assay of cells in vitro Nat. Protoc, published online Dec. 21, 2006, 1, 2315-2319.
Guertin, et al. "Defining the Role of mTOR in Cancer" Cancer Cell, Jul. 2007, 12, 9-22.
Hu, et al., "Antineoplastic Agents III: Steroidal Glycosides from Solanum nigrum," Planta Med. (Received Mar. 17, 1998) 1999, 65:35-38.

Ikeda, et al. "Steriodal Oligoglycosides from Solanum nigrum" Chem. Pharm. Bull. 2000, (received Feb. 21, 2000) 48, 1062-1064.
Ikeda, et al. "Cytotoxic Activity of Steroidal Glycosides from Solanum Plants" Chem. Pharm. Bull. 2003, (Received Feb. 3, 2003) 26, 1198-1201.
Klionsky, et al. (published online Apr. 1, 2012), Guidelines for the use and interpretation of assays for monitoring autophagy. Autophagy 8: 445-544.
Laladhas, et al. "A novel protein fraction from Sesbania grandiflora shows potential anticancer and chemopreventive efficacy, in vitro and in vivo" J. Cell. Mol. Med. 2011, (Received:Jul. 23, 2008) 14, 636-646.
Man, et al. "Chemical study and medical application of saponins as anti-cancer agents" Fitoterapia. 2010, (Received Jan. 20, 2010) 81, 703-714.
Marino, et al. (Feb. 2014). Self-consumption: the interplay of autophagy and apoptosis. Nat. Rev Mol. Cell Biol 15: 81-94.
Matter, et al. "Targeting the mTOR pathway in hepatocellular carcinoma:Current state and future trends" J. Hepatol. 2014,(Received Jul. 22, 2013): 60, 855-865.
Meijer, et al. "Regulation and role of autophagy in mammalian cells" Int. J Biochem Cell Biol (2004) (Received Nov. 25, 2003) 36: 2445-2462.
Melet, et al. "Apoptotic Pathways in Tumor Progression and Therapy" Adv. Exp. Med. Biol. 2008, 615, 47-79.
Milner, et al., "Bioactivities of Glycoalkaloids and Their Aglycones from *Solanum* Species," J. Agric. Food. Chem. (2011), (Received:Oct. 18, 2010) 59:3454-3484.
Mizushima,et al. "In vivo analysis of autophagy in response to nutrient starvation using transgenic mice expressing a fluorescent autophagosome marker" (Mar. 2004) MolBiol Cell 15: 1101-1111.
Mizushima,et al. "How to interpret LC3 immunoblotting" (2007) (Original manuscript submitted: May 24, 2007) Autophagy 3: 542-545.
Mizushima,et al. "Methods in mammalian autophagy research" (Feb. 5, 2010) Cell 140: 313-326.
Nyteler, et al. "Quantitative Visualization of Autophagy Induction by mTOR Inhibitors" (2012) Methods MolBiol 821: 239-250.
Perrone, et al., "Cytotoxic Furostanol Saponins and a Megastigmane Glucoside from Tribulus parvispinus," J. Nat. Prod. (2005), (Received Jun. 14, 2005) 68:1549-1553.
Pittelkow, et al., "New Techniques for the In Vitro Culture of Human Skin Keratinocytes and Perspectives on Their Use or Grafting of Patients With Extensive Bums," Mayo Clin Proc. (Oct. 1986), 61:771-777.
Podolak, et al. Saponinsas cytotoxic agents: a Review: Phytochem. Rev. 2010, 9, 425-474 (Received:Jan. 13, 2010/Accepted: Apr. 29, 2010/Published online: Jun. 25, 2010).
Raju, et al."Cancer Chemopreventive and Therapeutic Effects of Diosgenin, a Food Saponin," Nutr. Cancer. (2009), 61: 27-35 (Submitted Sep. 12, 2007).
Sun, et al. "NF-kappaB signaling, liver disease and hepatoprotective agents" Oncogene 2008, 27, 6228-6244.
Tanida, et al. "The human homolog of *Saccharomyces cerevisiae* Apg7p is a Protein-activating enzyme for multiple including human Apg12p, GATE-16, GABARAP, and MAP-LC3" (Jan. 19, 2001) J Biol Chem 276:1701-1706.
Trouillas, et al. "Structure-function relationship for saponin effects on cell cycle arrest and apoptosis in the human 1547 osteosarcoma cells: a molecular modelling approach of natural molecules structurally close to diosgenin," Bioorg. Med. Chem. (2005), 13:1141-1149 (Received Sep. 20, 2004, Available online Dec. 9, 2004).
Vincken, et al. "Saponins, classification and occurrence in the plant kingdom," Phytochemistry. (2007), 68:275-297 (Received Nov. 29, 2005, Available online Dec. 4, 2006).
Wang, et al. "Functional crosstalk between AKT/mTOR and Ras/MAPK pathways in hepatocarcinogenesis" Cell. Cycle. Jul. 1, 2013, 12, 1999-2010.
Wang, et al. "Growth inhibition and apoptosis-inducing effect on human cancer cells by RCE-4, a spirostanol saponin derivative from natural medicines" Int J Mol Med Jul. 1, 2013, 31, 219-224.

(56) References Cited

OTHER PUBLICATIONS

Wang, et al. "The novel mTOR inhibitor Torin-2 induces autophagy and downregulates the expression of UHRF1 to suppress hepatocarcinoma cell growth" Oncol. Rep. 2015, (Received Mar. 10, 2015) 34, 1708-1716.

Yang, et al. "Autophagy modulation for cancer therapy" (Jan. 15, 2011) Cancer BiolTher 11: 169-176.

Yu, et al. "Berberine-induced apoptotic and autophagic death of HepG2 cells requires AMPK activation" (2014) Cancer Cell Int 14: 49.

Zhou, et al. "Steroidal Saponins from Solanum nigrum" Nat. Prod. (Received Mar. 3, 2006) 2006, 69, 1158-1163.

Dash, S., et al., "Autophagy in hepatocellular carcinomas: from pathophysiology to therapeutic response," Hepatic Medicine: Evidence and Research, Feb. 22, 2016, pp. 9-20.

Hu, T., et al., "Chloroquine inhibits hepatocellular carcinoma cell growth in vitro and in vivo," Oncology Reports, vol. 35, 2016, pp. 43-49.

Kim, H.S., et al., "An Overview of Carcinogenic Heavy Metal: Molecular Toxicity Mechanism and Prevention," Journal of Cancer Prevention, vol. 20, No. 4, Dec. 2015, pp. 232-240.

Sobolewska, D., et al., "Steroidal saponins from the genus *Allium*," Phytochem Rev., Sep. 25, 2014, 35 pp.

Examination Report in corresponding European Application No. 17743096.4, dated Jul. 18, 2022.

\* cited by examiner

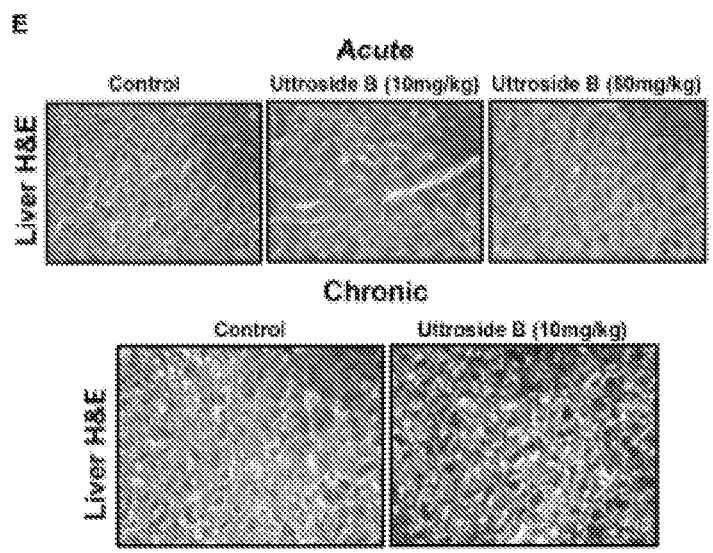
FIGURE 5E
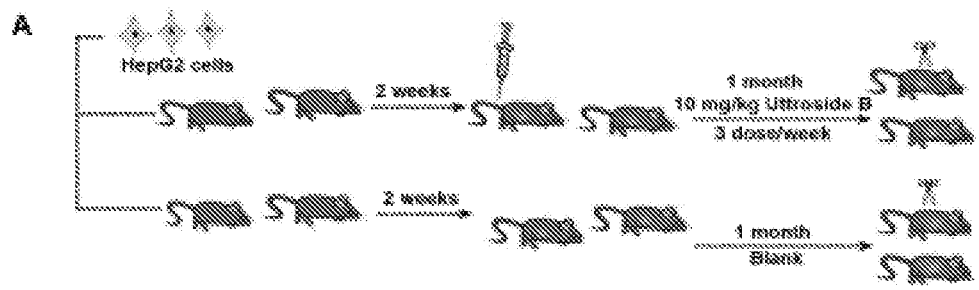
FIGURE 6A
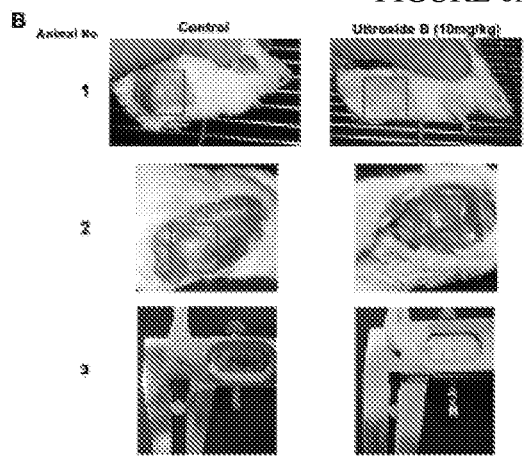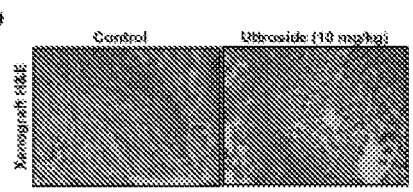
FIGURE 6B               FIGURE 6C

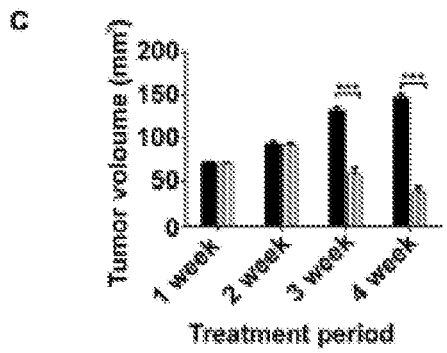
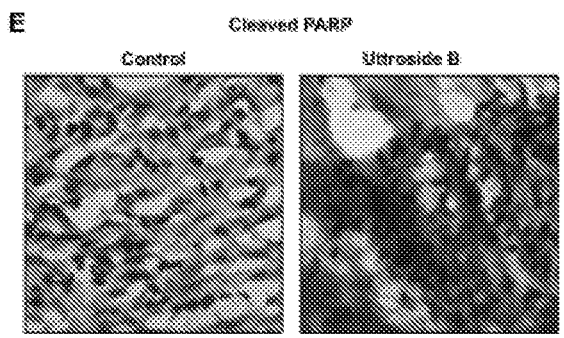
FIGURE 6D
FIGURE 6E
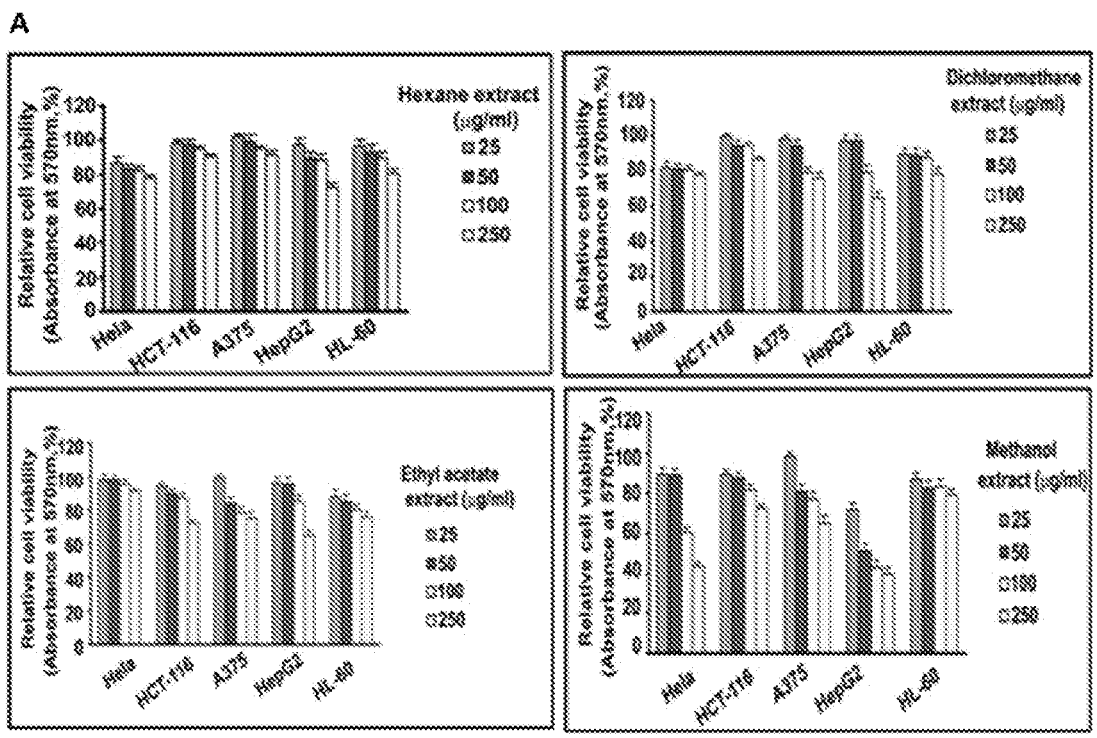
FIGURE 7A
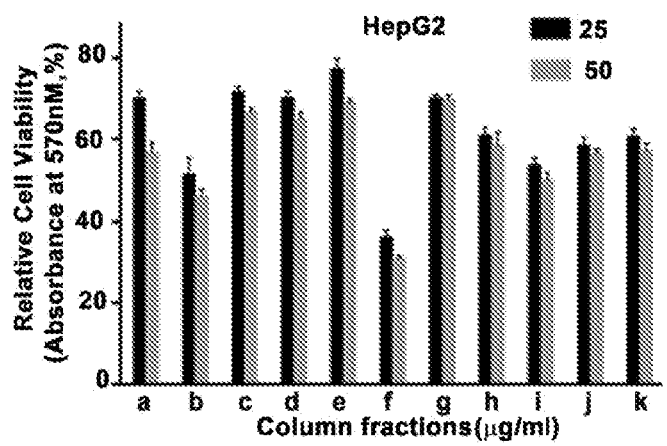
FIGURE 7B

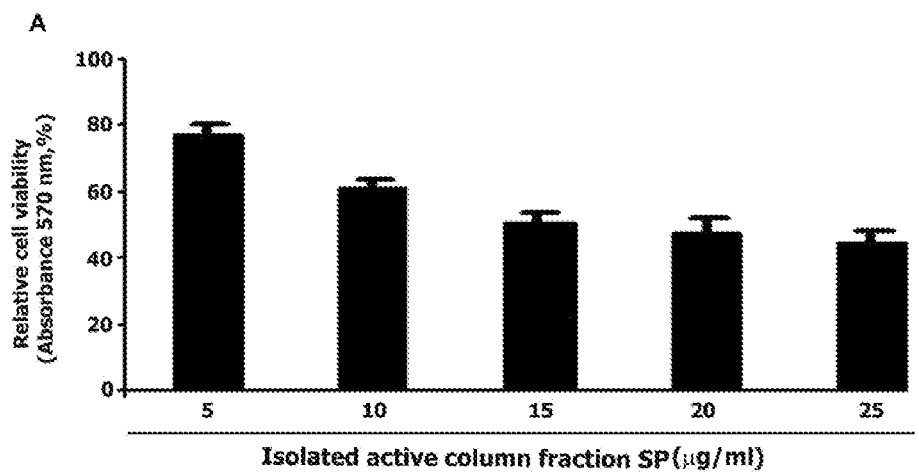
FIGURE 8A
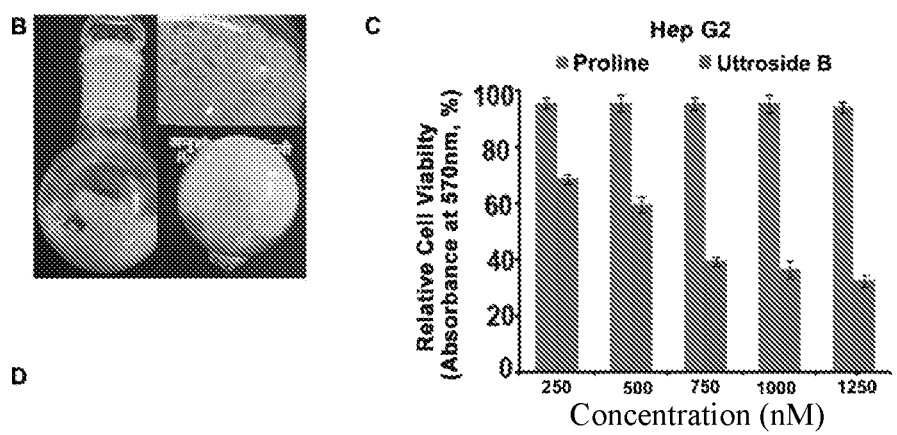
FIGURE 8B
FIGURE 8C
FIGURE 8D

SEQUENCE LISTING

```
<160> NUMBER OF SEQ ID NOS: 1

<210> SEQ ID NO 1
<211> LENGTH: 45
<212> TYPE: DNA
<213> ORGANISM: Artificial Sequence
<220> FEATURE:
<223> OTHER INFORMATION: Synthetic primer

<400> SEQUENCE: 1
ttgttacaag ggactttccg ctggggactt tccagggagg cgtgg                45
```

UTTROSIDE B AND DERIVATIVES THEREOF AS THERAPEUTICS FOR HEPATOCELLULAR CARCINOMA

CROSS-REFERENCE TO RELATED APPLICATIONS

This application a continuation of application Ser. No. 16/304,630, filed Nov. 26, 2018, which is the National Stage of International Application No. PCT/IN2017/050204, filed on 27 May 2017 claiming the priority of IN 201641018401 filed on 28 May 2016, the content of each of which is incorporated by reference herein.

TECHNICAL FIELD OF THE INVENTION

The present invention relates generally to novel saponins and derivatives thereof, methods of their preparation used as medicaments, particularly in cancer treatment.

BACKGROUND ART

Without limiting the scope of the invention, its background is described in connection with saponins and saponin derivatives. Triterpene and steroid glycosides commonly referred to as saponins, which are isolated primarily from the plant kingdom, exert a wide range of pharmacological properties owing to their large structural diversity[1]. Saponins form a large family of naturally occurring glycoconjugate compounds with considerable structural diversity. To the steroid, triterpenoid or steroidal alkaloid aglycone in these compounds a variable number of sugars is attached by the glycosidic bonds. The saponins display a broad spectrum of biological activities and practical applications.

U.S. Pat. No. 8,552,161 entitled, "Saponin Compounds, Methods of Preparation Thereof, Use Thereof and Pharmaceutical Compositions," discloses saponin compounds with a p-methoxybenzoyl substitution and a substitution with a C6-10 aryl, C6-10 aryl-C1-4 alkyl-, C1-18 alkanoyl, C3-18 alkenyl, C6-10 aryl-C(O)—, C6-10 aryl-C1-4 alkyl-C(O)—, wherein each of the groups can optionally be substituted. These compounds possess a selective cytostatic activity, useful, e.g., in the treatment of proliferative diseases.

U.S. Pat. No. 7,078,063 entitled, "Water Soluble Extract From Plant of *Solanum* Genus and the Preparation Process Thereof, and Pharmaceutical Composition Containing the Water Soluble Extract," discloses a water soluble extract from a plant of *Solanum* genus consists essentially of at least 60%-90% of solamargine and solasonine. A process for preparing the water soluble extract from the plant of *Solanum* genus involves the steps of hydrolysis with an acid, precipitation with a base, and separation treatments using chloroform, alcohol and water as extraction solvents. The water soluble extract prepared from the process can be directly dissolved in pure or neutral pH water to form a yellowish clear and transparent aqueous solution having a water solubility ranging from 2-20 mg/ml or higher.

SUMMARY OF THE INVENTION

Currently there are few compositions to treat hepatocellular carcinoma. Chemotherapeutic options for liver cancer are limited and the prognosis of HCC patients remains dismal. Sorafenib, derived from a de novo combinatorial approach by high-throughput screening and approved by US-FDA in 2007, is the only drug currently available for the treatment of hepatocellular carcinoma. Uttroside B, isolated from the leaves of *Solanum nigrum*, exhibited selective and significant cytotoxicity towards liver cancer cells (HepG2) with an IC50 value of 0.5 µM, which is more than 11.6 times less than that of sorafenib (IC50 5.8 µM), the only FDA approved drug for liver cancer. Such an exceptional selective and significant cytotoxicity towards liver cancer cells (HepG2) is both surprising and unexpected. Uttroside B induces apoptosis in HepG2 cells and down-regulates MAPK and mTOR pathways, among the various cell survival signaling pathways evaluated. The biological safety of the compound was evaluated in vitro in the normal immortalized hepatocytes (Chang liver cells) and in vivo using both acute and chronic toxicity models in Swiss albino mice. In vivo studies using HepG2-xenograft model in NOD-SCID mice also establish the anticancer efficacy of this molecule against liver cancer. These results showcase Uttroside B as a pharmacologically safe drug which warrants further clinical validation against hepatic cancer, a tumor against which the chemotherapeutic armamentarium currently has very few weapons.

The present invention provides a composition for the treatment of a hepatocellular carcinoma, wherein the composition comprises: a pharmaceutically effective amount of Uttroside B disposed in a pharmaceutical carrier. The present invention provides a method of increasing the stability of an Uttroside B composition comprising the steps of adding proline to the Uttroside B composition. The present invention provides a composition for inhibiting tumor growth, wherein the composition comprises: a pharmaceutically effective amount of Uttroside B disposed in a pharmaceutical carrier. The present invention provides an Uttroside B composition for the treatment of a liver cancer by inducing apoptosis, down-regulates MAPK pathway, down-regulates mTOR pathway or a combination thereof wherein the Uttroside B composition comprises: a pharmaceutically effective amount of Uttroside B disposed in a pharmaceutical carrier. The present invention provides a composition for the treatment of a liver disease wherein the composition comprises: a pharmaceutically effective amount of Uttroside B disposed in a pharmaceutical carrier. The present invention provides an Uttroside B composition for use as a medicament for the treatment of a liver disease wherein the composition comprises: a pharmaceutically effective amount of Uttroside B; disposed in a pharmaceutical carrier.

The present invention is used to treat liver disease in any form or state and includes but is not limited to liver sclerosis, Nonalcoholic Steatohepatitis (NASH), non-alcoholic fatty liver disease (NAFLD), Cirrhosis, or Primary Biliary Cholangitis. Similarly, the present invention is used to treat liver cancer in any form or state and includes but is not limited to a hepatocellular carcinoma (HCC), Fibrolamellar carcinoma, Cholangiocarcinoma (bile duct cancer), Angiosarcoma, or Hepatoblastoma.

Any of the compositions and medicaments may further comprising stability agents including proline, preferably a proline oligomer and most preferably free proline. Any of the compositions and medicaments may further include one or more glutathiones, optionally one or more oligomers of glutathiones or phytochelatins.

The present invention can be combined with other treatments as a single dose, multiple doses, sequential doses, with one or more active agents, e.g., sorafenib disposed in the pharmaceutical carrier.

Similarly, the Uttroside B has a concentration of about range of between 0.05 and 150 mg/kg body weight, preferably between 5 and 80 mg/kg body weight, more preferably between 10 and 50 mg/kg body weight and most preferably about 10 mg/kg body weight. The Uttroside B concentration may be increased as agents are added to the pharmaceutical carrier to increase stability and reduce the activity of the Uttroside B. In some instances the may be 75-125 mg/body weight. The Uttroside B has a concentration of about range of between 0.66 µM and 2 mM, preferably between 0.066 and 1.32 mM, and most preferably between 0.132 and 1.05 mM.

BRIEF DESCRIPTION OF THE DRAWINGS

For a more complete understanding of the features and advantages of the present invention, reference is now made to the detailed description of the invention along with the accompanying figures and in which:

FIGS. 5A-5E show toxicological evaluation of Uttroside B in Swiss Albino mice.

FIG. 6A is a pictorial representation illustrating the antitumor study. FIG. 6B are representative photographs of mice bearing HepG2 xenograft tumors with or without Uttroside B treatment after four weeks. FIG. 6C is a graph showing Uttroside B effectively inhibits the tumor volume in NOD-SCID mice model. FIG. 6D is an image of a histopathological evaluation of tumor tissue isolated from control and Uttroside B-treated group of NOD-SCID mice. FIG. 6E is an image of Uttroside B induces apoptosis in Uttroside-treated tumor sections.

FIG. 7A is a graph of the cytotoxicity of organic extracts of *S. nigrum* in a panel of five cancer cell lines. FIG. 7B is a graph of the cytotoxicity induced by *S. nigrum* isolated column fractions, in HepG2 cells. HepG2 cells were treated with different concentrations of column fractions as indicated and cell viability was assessed by MTT.

FIG. 8A is a graph of the dose dependent cytotoxicity induced by mixture of saponin and proline (SP) in HepG2 cells. FIG. 8B is an image of a pale yellow foamy solid, mixture of proline and saponin. FIG. 8C is a graph of the cytotoxicity of isolated saponin and proline in a dose dependent manner. FIG. 8D is an image of Uttroside B (1) is a white solid.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The technology is related to use of Uttroside B (isolated from *Solanum nigrum* plant) as a treatment of hepatocellular carcinoma. Current treatments of hepatocellular carcinoma include: radiation (internal or external), chemoembolization, alcohol injection, ablation (cryo or RF), and surgery/transplant. The only currently available oral, therapeutic treatment is NEXAVAR™ (sorafenib) produced by Bayer & Onyx Pharmaceuticals, which is a tyrosine protein kinase inhibitor.

A vast array of saponins have been reported to exhibit anti-tumor effect against a wide panel of cancer cells.[2-3] In natural product research, the chemotherapeutic efficacy of saponins against various cancer cells is confined to in vitro data with specific emphasis towards their structure elucidation.[3] Various plant species of *Solanum* genera were found to have considerable amount of saponins, which exhibit potent anticancer activity against different cancer cell lines.[4,5] *Solanum nigrum*, commonly known as black nightshade, is a medicinal plant member of Solanaceae family, widely used in many traditional systems of medicine.[6] Alcoholic extract of the whole plant has been reported to contain various steroidal saponins, which induce cytotoxicity in different cancer cell lines.[7-9] Sharma et. al. have reported two furostanol saponins, Uttroside A and B, from the methanolic extract of the stems and roots of *S. nigrum*.[10]

Figure 1:
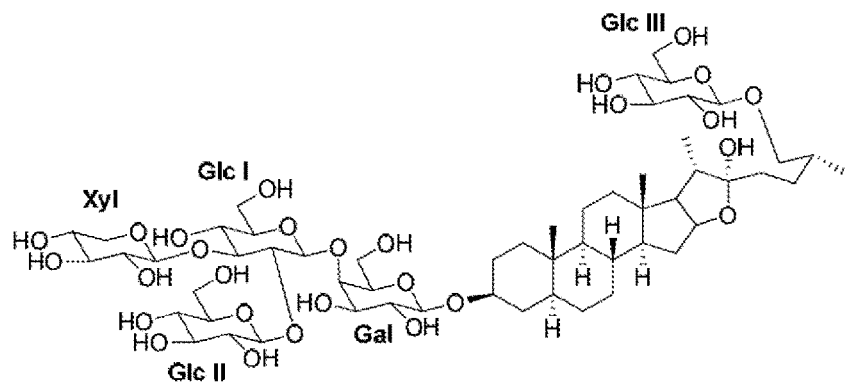
FIG. 1 is an image showing the structure of Uttroside B.

FIG. 1 is an image showing the structure of Uttroside B. Uttroside B is characterized by the presence of β-D-glucopyranosyl unit at C-26 of the furostanol and β-lycotetraosyl unit at C-3. The compound has also been isolated from *Tribulus terrestris*[11] and *Polianthes tuberosa*[12] and has been shown to exhibit significant cytotoxicity against PC-12 (IC50 1.20 µM) and HCT-116 (IC50 2.33 µM) cells[13] and moderate cytotoxicity (IC50 15.43 µM) against HeLa cells[12]. Parvispinoside B, another saponin isolated from *Tribulusparvispinus*, which structurally differs from Uttroside B by just one sugar in the lycotetraosyl unit, exhibits strong cytotoxicity against the U937 leukemia cell line (IC50 0.5 µM), while not effective against HepG2 cells (IC50>100 µM).[14] However, in the present study, Uttroside B exhibits maximum cytotoxicity against HepG2 cells (IC50 0.5 µM), which is more than ten times effective than sorafenib (IC50 5.8 µM), the only FDA approved drug for liver cancer. The cytotoxicity of Uttroside B in HepG2 cells is through induction of apoptosis and confirmed its biological safety by both in vitro (normal Chang liver cells) and in vivo studies. The anticancer potency of this molecule was further proven in vivo using HepG2-Xenograft model in NOD-SCID mice.

Figure 2A:
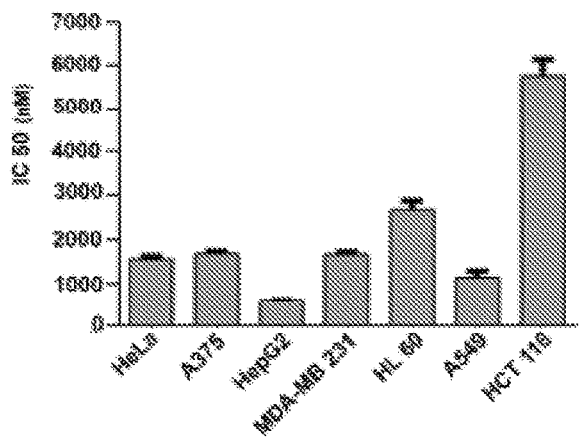
FIGS. 2A-2F illustrate that Uttroside B shows maximum sensitivity towards liver cancer cells.
Figure 2B:
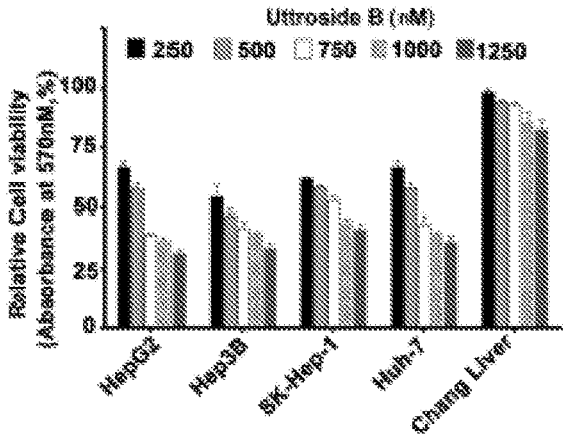
Figure 2C:
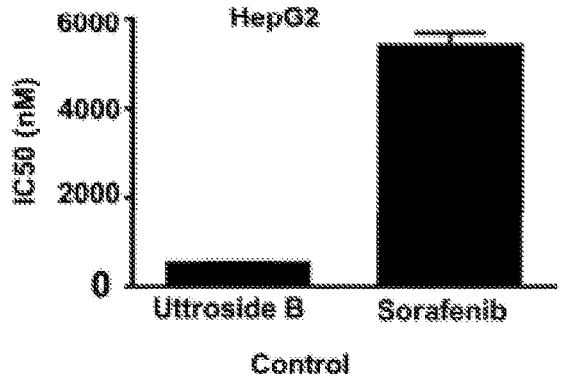
Figure 2D:
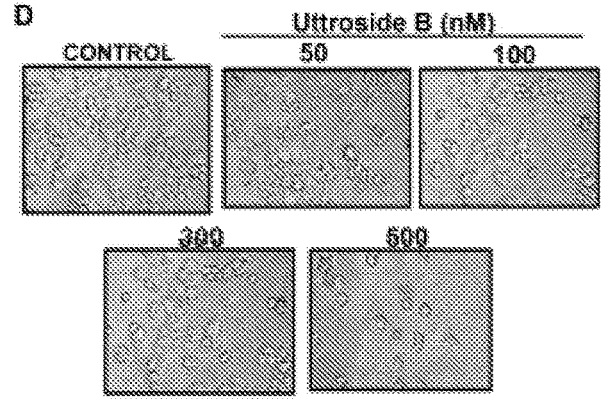
Figure 2E:
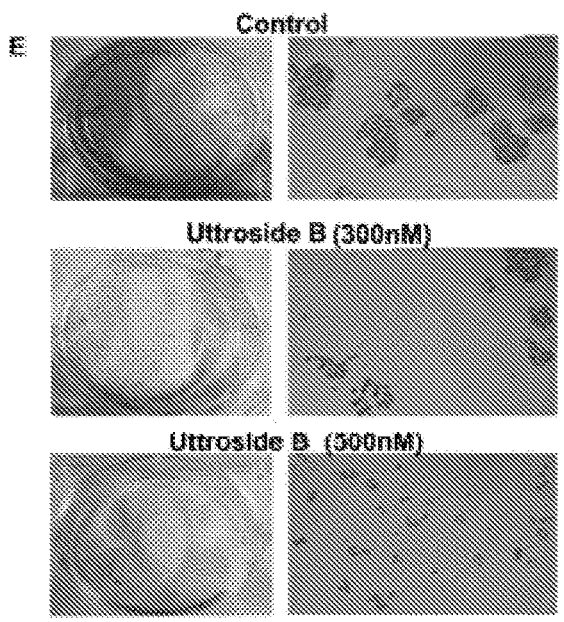
Figure 2F:
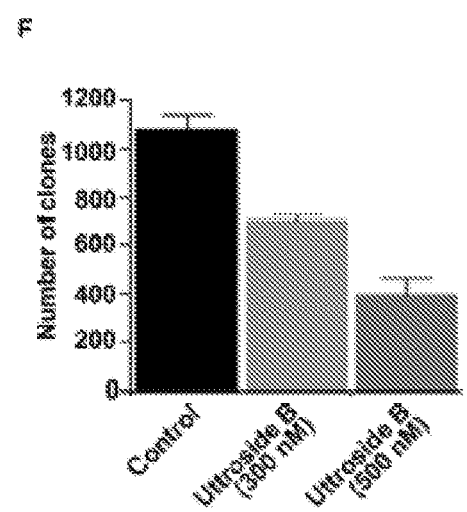

FIGS. 2A-2F illustrate that Uttroside B shows maximum sensitivity towards liver cancer cells. FIG. 2A is a graph comparison of IC50 of Uttroside B in a panel of cancer cells of different origin. The cancer cell lines HeLa, A375, HepG2, MDA-MB-231, HL 60, A549 and HCT116 were treated with Uttroside B as indicated, incubated for 72 h and the cell viability was assessed by MTT assay. FIG. 2B is a graph showing dose dependent effect of Uttroside B in the liver cancer cell lines and in normal immortalized hepatocytes. The liver cancer cell lines HepG2, Hep3B, SKHEP-1, Huh-7 and normal hepatocytes (Chang liver), were treated with Uttroside B incubated for 72 h and the cell viability was assessed by MTT assay. FIG. 2C is a graph comparison of IC50 of Uttroside B with sorafenib. HepG2 cells were treated with Uttroside B as indicated, incubated for 72 h, and the cell viability was assessed by MTT assay. FIG. 2D is an image of the morphological changes induced by Uttroside B in HepG2 cells. HepG2 cells were treated with Uttroside B as indicated and incubated for 72 h. FIG. 2E is an image showing Uttroside B inhibits the clonogenic potential of HepG2 cells. HepG2 cells were treated with different concentrations of Uttroside B for 72 h and the clonogenic assay was performed. FIG. 2F is a graph comparison of efficacy of Uttroside B in inhibiting the clonogenic potential of HepG2 cells. The clones developed were counted and plotted as a graph. Colony containing more than four cells was counted as one clone.

It was very interesting to note that the HepG2 (liver cancer) cells were showing maximum sensitivity to this compound with an IC50 of 0.5 µM followed by A549 (1 µM), HeLa (1.5 µM), A375 (1.6 µM), MDA-MB-231 (1.6 µM), HL60 (2.5 µM), and HCT-116 (6 µM) [FIG. 2A]. The next attempt was to compare the effect of Uttroside B in different hepatocellular carcinoma cells (HepG2, Hep3B, SKHep1, and Huh-7) and normal immortalized hepatocytes (Chang liver) using MTT assay. While there was no drastic difference observed between any of the liver cancer cells for their sensitivity towards Uttroside B (IC50: 400-600 nM), 70% of the normal immortalized hepatocytes (Chang Liver) were viable even at 1250 nM [FIG. 2B]. Taken together, it was revealed that Uttroside B is effective against liver cancer cells at nanomolar concentrations while being non-toxic to normal immortalized hepatocytes. HepG2, the most sensitive among the panel of cell lines was selected for further studies. The cytotoxicity of Uttroside B was compared with that of sorafenib, the only FDA approved drug against liver cancer. Surprisingly, Uttroside B was more than ten times potent than sorafenib in killing liver cancer cells [FIG. 2C]. HepG2 cells were examined for morphological changes by Phase contrast microscopy, 72 h after treatment with Uttroside B. Nuclear condensation, membrane blebbing and formation of apoptotic bodies, which are characteristics of apoptosis was observed in a dose dependent manner in the Uttroside B-treated HepG2 cells, compared to untreated controls [FIG. 2D]. Uttroside B was also studied for its anti-clonogenic potential in HepG2 cells in a concentration dependent manner. Clonogenic assay is an in vitro assay routinely used as a technique for studying the effectiveness of specific agents on the survival and proliferation of cells.[15,16] The drastic dose dependent reduction in both number and size of the colonies formed, demonstrates the anti-clonogenic potential of Uttroside B [FIGS. 2E-2F].

Figure 3A:
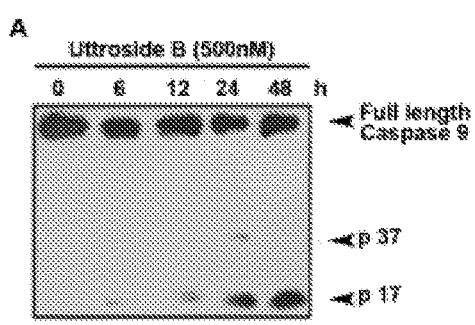
FIGS. 3A-3E are images of Western blots showing caspase activation in HepG2 cells.
Figure 3B:
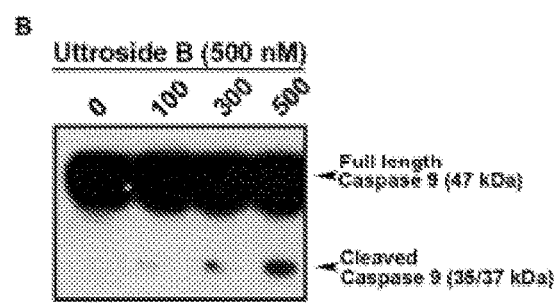
Figure 3C:
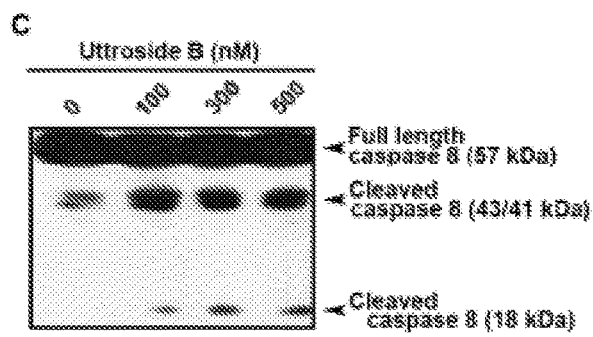
Figure 3D:
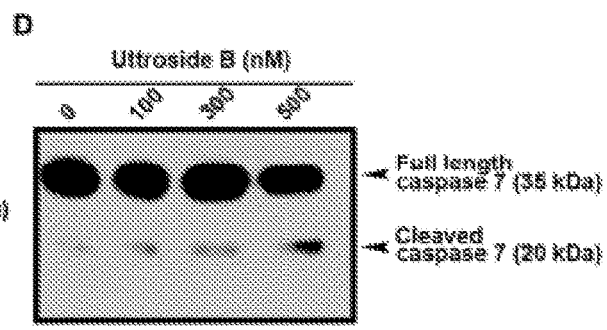
Figure 3E:
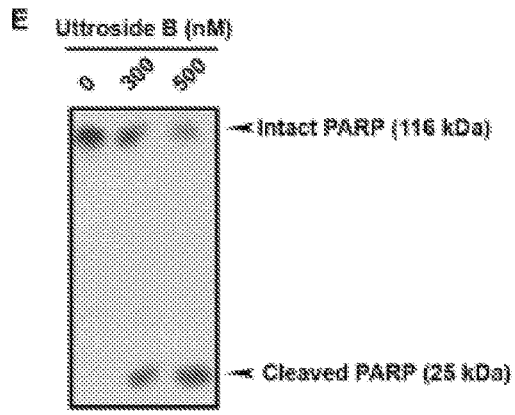
Figure 3F:
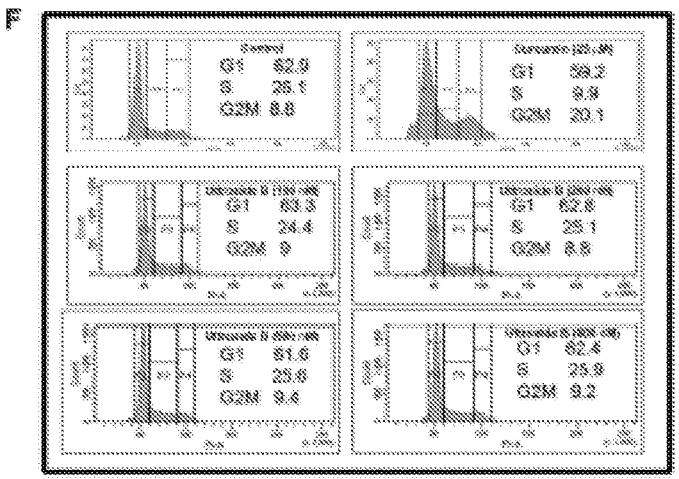
FIG. 3F is an image that shows Uttroside B does not affect any phases of cell cycle in HepG2 cells.

FIGS. 3A-3F show Uttroside B induces caspase-dependent apoptosis leading to PARP cleavage in HepG2 cells while being independent of cell cycle. FIGS. 3A-3E are images of Western blots showing caspase activation in HepG2 cells. Whole-cell extracts were prepared after treating HepG2 cells with indicated concentrations of Uttroside B for 48 h, the whole cell lysate was resolved on a 15% gel and subjected to western blotting using antibodies against the caspases 8, 9 & 7 detected by ECL. HepG2 cells were treated with Uttroside B for 48 h at different concentrations and the whole cell lysate was resolved on a 10% gel, immunoblotted against anti-PARP and detected by ECL. FIG. 3F is an image that shows Uttroside B does not affect any phases of cell cycle in HepG2 cells. HepG2 cells were treated with Uttroside B for 48 h, stained with propidium iodide and the cell cycle analysis was done using fluorescence activated cell sorter. Curcumin 25 μM (24 h) is used as positive control.

Uttroside B induces apoptosis in HepG2 cells, while not influencing any phase of the cell cycle. Apoptosis analysis was conducted using Western blot method. Uttroside B was found to exhibit time-dependent and concentration-dependent increase in the cleavage of procaspase 9, an initiator caspase to its active fragments (p35/37 and p17) [FIG. 3A]. A strong induction of caspase activation appears after 24 h and is peaked at 48 h. The analysis of remaining caspases and their downstream target were carried out after 48 h in a concentration dependent manner. As observed previously, an increase in the cleavage of procaspase 9, an initiator caspase, to its active fragments (p35/37 and p17) [FIG. 3B], an increase in the cleavage of procaspase 8 to its active fragments (p43/41) [FIG. 3C], and procaspase 7 into its active fragment (p-20) were also enhanced due to Uttroside B treatment after 48 h in a concentration dependent manner [FIG. 3D]. As expected, Uttroside B induced cleavage of PARP, a downstream event of caspase activation. In the Uttroside B treated cells, there was a strong cleavage of the mother band to its daughter bands, where the 89 kDa daughter band was completely degraded to 25 kDa, while in the control cells the mother band 116 kDa PARP remained intact [FIG. 3E]. The distribution of a given population of cells to different stages of cell cycle can be assessed by quantitative measurement of nuclear DNA content by flow cytometry analysis. The treatment of HepG2 cells with Uttroside B did not show any significant effect on cell cycle at any of the concentrations studied even after 48 h, while the positive control (25 μM) curcumin readily induced cell cycle arrest at G2/M after 24 h [FIG. 3F].

Figure 4A:
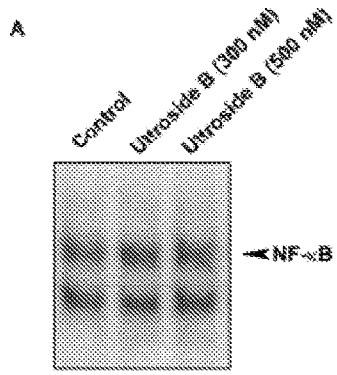
FIGS. 4A-4E are images showing Uttroside B inhibits MAPK and mTOR signaling, some of the crucial survival signals in liver cancer.
Figure 4B:
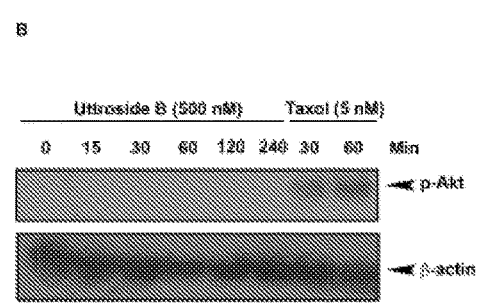
Figure 4C:
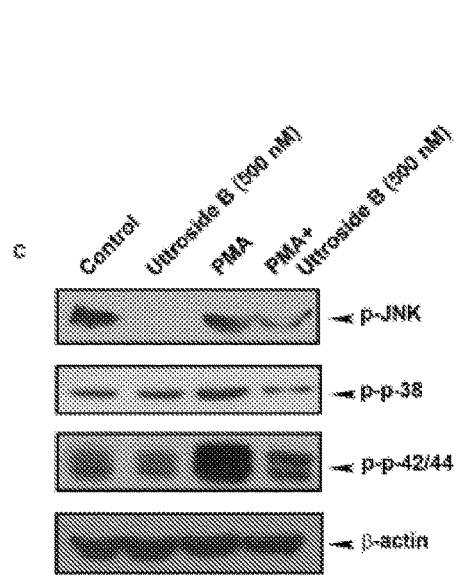
Figure 4D:
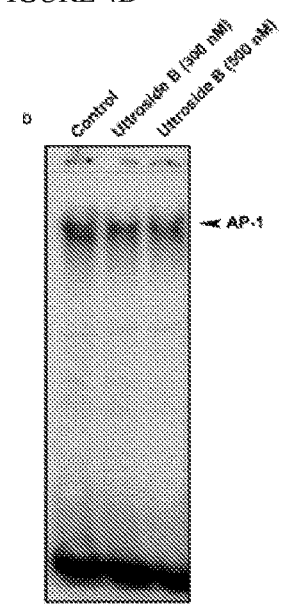
Figure 4E:
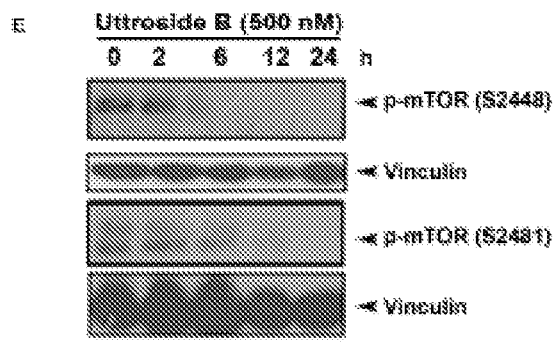

FIGS. 4A-4E are images showing Uttroside B inhibits MAPK and mTOR signaling, some of the crucial survival signals in liver cancer. FIG. 4A shows Uttroside B does not have any role in nuclear translocation of NF-κB. FIG. 4B shows kinetics of Uttroside B-induced phosphorylation of Akt in HepG2 cells. HepG2 cells were treated with Uttroside B for different time intervals (0-240 min) and the whole cell lysate was resolved on a 10% gel and immunoblotted against phospho-ERK1/2 and phospho-Akt antibodies. Taxol was used as a positive control. FIG. 4C shows Uttroside B down-regulates the constitutive and PMA-induced phosphorylation of P-JNK, P38 & ERK1/2. FIG. 4D shows Uttroside B significantly down-regulates the nuclear translocation of AP-1. FIG. 4E shows kinetics of Uttroside B-induced phosphorylation of mTOR induced by Uttroside B in HepG2 cells. HepG2 cells were treated with Uttroside B at different time intervals and the whole cell lysate was resolved on an 8% gel and immunoblotted against phospho-mTOR (2448) and phospho-mTOR (2481) antibodies.

Effect of Uttroside B in regulating various survival signals prevalent in cancer progression. To find out the regulatory molecules associated with some of the major signaling events associated with cancer progression, HepG2 cells were treated with Uttroside B, the nuclear extracts and whole cell extracts were prepared. Though there was a constitutive activation of NF-κB in HepG2 cells, Uttroside B could not produce any significant down-regulation of the same as assessed by the electrophoretic mobility shift assay (EMSA, FIG. 4A). Activation status of Akt was also assessed in these cells by Western Blot. However, no basal activation of Akt was observed in HepG2 and hence, Uttroside B had no significant role in activating Akt pathway (FIG. 4B). Interestingly, the basal activation of MAPK pathway was evident in these cells, which was significantly down-regulated by Uttroside B, especially p-42/44 and p-JNK signaling. Moreover, PMA-induced activation of p-JNK, p-38 and p-42/44 was also down-regulated by Uttroside B indicating a significant role for this pathway in regulating the anticancer potential of Uttroside B against liver cancer [FIG. 4C]. Supporting this observation, AP-1, the downstream target of MAPK signaling was also down-regulated by Uttroside B as assessed by electrophoretic mobility shift assay [FIG. 4D]. mTOR pathway is a major survival signal, which plays a pivotal role in cell growth and metabolism and is up-regulated in almost 50% of liver cancer. A strong basal activation of this pathway was observed in HepG2 cells. We checked whether Uttroside B can down-regulate this activated mTOR by Western blot analysis. It was very interesting to see a time dependent decrease in the phosphorylation of m-TOR at 2448 and 2481 phosphorylation sites, a read out of p-mTOR activation on Uttroside B exposure [FIG. 4E].

Figure 5A:
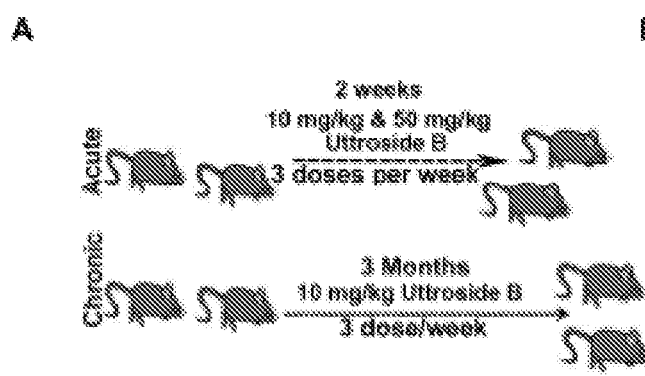
Figure 5B:
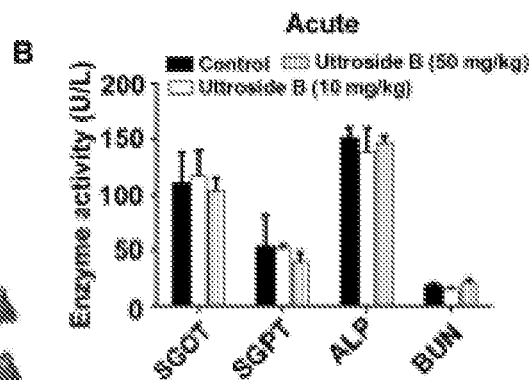
Figure 5C:
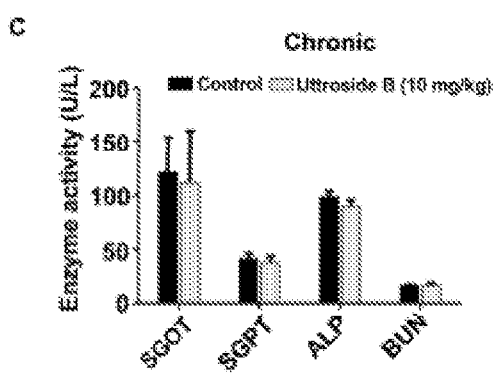
Figure 5D:
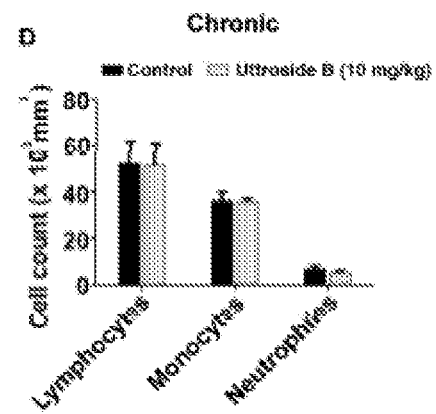

FIGS. 5A-5E show toxicological evaluation of Uttroside B in Swiss Albino mice. FIG. 5A is a schematic representation of toxicity studies using Uttroside B in Swiss albino mice. FIGS. 5B-5D shows (B-D) serum biochemical analysis of Uttroside B illustrates it does not induce any hepatotoxicity, haematotoxicity, and nephrotoxicity as assessed by acute and chronic toxicity studies. Uttroside B does not induce liver toxicity as assessed by liver histopathological analysis as seen in FIG. 5E. Histopathological evaluation of tumor tissue isolated from control and Uttroside B treated group of Swiss Albino mice. Formalin fixed cryosections were stained with haematoxylin and eosin.

Uttroside B is pharmacologically safe as assessed by acute and chronic toxicity model. To rule out the possibility of any toxic side effects due to Uttroside B, a detailed toxicological evaluation of the compound was conducted in Swiss albino mice as shown in FIG. 5A.

The group of mice, which received 10 mg/kg and 50 mg/kg dose of Uttroside B did not exhibit any abnormal behavior and did not show any deviation in the serum levels of AST [(Aspartate aminotransferase, SGOT)], ALT [(Alanine transferase, SGPT)] and ALP (Alkaline phosphatase) [FIG. 5B] which are clear markers of abnormality in liver function. In chronic cytotoxic study of 3 months, the haematotoxicity, hepatotoxicity and nephrotoxcity due to Uttroside B was assayed by analyzing the level of total and differential count of WBC and serum levels of AST, ALT, ALP and BUN (blood urea nitrogen), respectively in control and treated mice [FIG. 5C-5D]. The results indicate that there was no significant difference in any of these parameters from their normal range of values, demonstrating that Uttroside B is pharmacologically safe and nontoxic. The histopathological analysis of liver tissue isolated from mice in the acute(10 mg/kg and 50 mg/kg) and chronic toxicity studies (10 mg/kg), used the same dose of Uttroside B which was used for the tumor reduction studies, did not manifest any morphological change characteristic of toxicity. In the liver tissues of acute toxicity study, at five times higher amount of the treatment dose (50 mg/kg), micro vesicular fatty changes were exhibited which are reversible changes associated with any chemotherapy. These observations confirm that Uttroside B can be safely used as a chemotherapeutic drug for being validated through pre-clinical trials [FIG. 5E].

FIG. 6: Uttroside B inhibits development of hepatic xenograft tumor in NOD-SCID mice. FIG. 6A is a pictorial representation illustrating the anti-tumor study. FIG. 6B are representative photographs of mice bearing HepG2 xenograft tumors with or without Uttroside B treatment after four weeks. FIG. 6C is a graph showing Uttroside B effectively inhibits the tumor volume in NOD-SCID mice model. The average volume of HepG2 xenograft tumors among control and Uttroside B treated group are shown. Data shows the average of three independent set of studies with 9 animals per group (P-values<0.005). FIG. 6D is an image of a histopathological evaluation of tumor tissue isolated from control and Uttroside B-treated group of NOD-SCID mice. Formalin fixed cryosections were stained with haemotoxylin and eosin. FIG. 6E is an image of Uttroside B induces apoptosis in Uttroside-treated tumor sections: IHC analysis of tumor cryosections of control Uttroside B-treated mice using cleaved PARP antibody and the expression of cleaved PARP was detected in tumor tissue sections from mice treated with Uttroside B, illustrating apoptosis.

Our next attempt was to validate the anticancer potential of Uttroside B against hepatic cancer, using an in vivo HepG2-xenograft model in NOD-SCID mice. The HepG2 cells suspended in matrigel were subcutaneously injected in the flank region of the mice. The study has been schematically represented in FIG. 6A. Uttroside B, dissolved in PBS, was administered after 15 days of tumor cell implantation when the tumor attained a size of 50-100 mm$^3$ approximately. Uttroside B (10 mg/kg bw) was injected intraperitoneally, thrice weekly for four weeks. Group 1 comprises of control animals, which did not receive any treatment. The size of the tumor was measured using Vernier calipers every week and the corresponding tumor volume was calculated. The volume of tumor developed in animals that received Uttroside B is significantly low comparing to that of the control mice which were injected the vehicle. At the end of the treatment period, no tumor was visible externally in the group of mice which received Uttroside B, whereas in the control group measurable tumor was developed. However, upon sacrifice, very small tumors were observed beneath the skin of animals treated with Uttroside B too, though the size was drastically less compared to that of control animals [FIG. 6B-6C]. The tumor mass developed was histopathologically analyzed using H&E staining, which also indicates a massive destruction of cells in Uttroside B-treated tumor tissue, which correlates with the drastic tumor reduction [FIG. 6D]. IHC staining of the formalin fixed cryosections of ectopically implanted human liver xenografts in NOD-SCID mice against cleaved PARP specific antibody revealed the in vivo apoptotic response of Uttroside B. Significant upregulation in the expression of cleaved PARP was observed in tumor sections from mice treated with Uttroside B [FIG. 6E]. Although this study was in a mouse the skilled artisan knows that that dose may be converted to human equivalent dosage by simple math. For example the 10 mg/kg body weight for a mouse would convert to a 0.8 mg/kg body weight for a human and result in a range from 0.05 to 1.2 mg/kg body weight.

Several studies demonstrate that many traditional medicines containing bioactives from plants exhibit anti-tumor effects and have been used for treating different types of cancer.[17-20] There are reports which indicate the use of saponins as anticancer agents.[3,21] RCE-4, (1β,3β,5β,25S)-spirostan-1,3-diol1-[α-L-rhamnopyranosyl-(1→2)-β-Dxylopyranoside], a spirostanol saponin derivative isolated from Reineckia carnea has been shown to induce growth inhibition and apoptosis in human cancer cells.[22] Degalactotigonin (1059 Da) is a highly cytotoxic (0.25 µM) saponin known from S. nigrum.[9] There are few reports, which exist in literature regarding the cytotoxic potential of Uttroside B against cervical and colon cancer cells,[12,13] with a relatively higher IC50 values (15.43 µM and 2.33 µM, respectively) though no further information has been reported regarding its biological safety or mechanism of action. To the best of our knowledge, this is the first study reporting the exceptional anticancer potential of Uttroside B against hepatocellular carcinoma, while being pharmacologically safe and non-toxic to normal liver cells. An ideal chemopreventive agent should be nontoxic, effective at lower doses, economical and easily available.[23] Even though S. nigrum is an important herb used in the Indian traditional system of medicine and several molecules isolated from it have been extensively studied for their anticancer potential, the anticancer potential of Uttroside B a 1215.12 Da saponin isolated from this plant has not been explored much. As per our observation, Uttroside B is most cytotoxic to liver cancer cells, even though it induces cytotoxicity in other cancer cells too. The present study also revealed that Uttroside B inhibits the clonogenic potential of HepG2, a liver cancer cell line. Most of the chemotherapeutic agents act mainly by inducing apoptosis in cancer cells. The efficiency of chemotherapy depends on the successful induction of apoptosis, since defects in apoptosis signaling are a major cause of drug resistance.[24] Apoptosis is a cascade of molecular events characterized by the activation of caspases, which are synthesized as zymogens (procaspases) whose proteolytic cleavage in response to chemotherapeutic agents leads to their activation. The apoptotic program begins with activation of initiator caspases, followed by executioner caspases, which subsequently leads to the cleavage of functional enzymes such as PARP in a sequential order, thus helping in the systematic dismantling of tumor cells without causing toxicity or inflammation to the surrounding tissues. In concordance with the currently acceptable dogma regarding apoptosis, Uttroside B was found to induce such signature molecular events in hepatic cancer cells and brought about a time-dependent cleavage of caspase 9, an initiator caspase, into its active fragments, and the cleaved fragments appeared at 24 h and peaked at 48 h, which prompted us to analyze the remaining caspases and its downstream target at 48 h. Once activated, caspase-9/8, the initiator caspases activate caspase-3/7, the effector caspases thereby promoting the execution of apoptotic cell death. During apoptosis, the DNA repair enzyme Poly(ADPRibose) polymerase (PARP) most often undergoes proteolytic cleavage by caspase-3 or caspase-7 and the native 116 kDa is cleaved into 89 kDa fragment containing the COOH terminal catalytic domain and a 25 kDa fragment containing truncated NH2-terminal DNA binding domain. PARP cleavage is considered as one of the important markers of caspase activation. Uttroside B induced all classical markers of caspase-dependent apoptosis, as evidenced by presence of apoptotic bodies, cleavage of caspases and PARP. Induction of cell cycle arrest is another mechanism through which chemotherapeutic drugs induce cytotoxicity in cancer cells. Reports indicate that some steroidal saponins such as diosgenin, and smilagenin block cell cycle in G0/G1 phase, while some others like tigogenin has no effect on cell cycle, which indicate that the difference in the spatial conformation of the A- and B-rings and the presence or lack of 5, 6-double bond are not the determinants of the mode of action of the saponin on the cell cycle.[3,25] Results of our study confirm that Uttroside B does not have any effect on the cell cycle like tigogenin. The mechanism of tumor survival in HCC, which involves multiple signaling mechanisms that regulate its growth, is highly complex. NF-κB, Akt, MAPK, and mTOR are the most prevalent survival signals promoting the progression of hepatic cancer and most of the drugs targeting hepatic cancer are inhibitors of these pathways.[26,27] Uttroside B could not produce any significant down-regulation in the constitutive activation of NF-κB in HepG2 cells. Another interesting observation was the absence of activated Akt in HepG2 cells, which made us exclude Akt also from the list of possible pathways regulating the anticancer potential of Uttroside B. However, basal level phosphorylation of both MAPKs and mTOR, which are constitutively activated in these cells are completely abolished by Uttroside B implicating a strong role for both these pathways in regulating Uttroside B-induced cytotoxicity in HepG2. Uttroside B also down-regulated PMA-induced phosphorylation of all members of MAPK pathway (JNK, p38 and p42/44). Reports indicate that the mammalian target of rapamycin (mTOR) pathway is abnormally activated in a proportion of HCC patients and inhibition of mTOR can suppress liver tumor growth and metastasis.[28,29] Moreover, an up-regulation of mTOR is frequently observed in cholangiocarcinoma, the second most common primary cancer of the liver.[30] A complex interplay between mTOR and MAPK pathways has also been demonstrated during hepatocarcinogenesis.[31] However, more studies are required to see whether both these pathways are dependent or independent of each other in regulating the anticancer potential of Uttroside B. The biological safety of Uttroside B was carried out in Swiss albino mice using short term (7 days) and long term (3 months) toxicity studies. Almost all currently available chemotherapy schemes for the treatment of cancer are associated with considerable toxicities that fail to transcend into optimal clinical benefits for patients. The major problem associated with chemotherapy is the reduction in the count of hematological parameters such as lymphocytes, neutrophils and monocytes. Uttroside B did not produce any significant difference in hematological parameters indicating that it does not cause any toxicity or immunosuppression in animals. Following the onset of liver damage, ALP (SGPT), AST (SGOT) and ALT are released from the damaged cells, elevating their levels in the serum. The level of the liver function enzymes in the serum of animals in both acute and chronic toxicity studies were in the normal range, suggesting that Uttroside B is non-toxic and pharmacologically safe in vivo. The normal level of blood urea nitrogen (BUN) also indicated that Uttroside B is not producing any severe toxicological manifestations in the kidney. Uttroside B, up to 5 times dose, failed to exhibit any signs of cumulative adverse response in study animals as concluded from gross measures such as loss of body weight, ruffling of fur and change in behavior and food intake indicating that the Uttroside B is pharmacologically safe for in vivo administration. The drastic inhibition of tumor growth produced by UttrosideB in NOD-SCID mice having human liver cancer xenografts illustrates and underscores the chemotherapeutic efficacy of Uttroside B, which was further authenticated by immunohistochemical analysis of the tumor sections for the expression of cleaved PARP, the significant presence of which is a clear marker of apoptosis.

Chemotherapeutic options for liver cancer are limited and the prognosis of HCC patients remains dismal. Sorafenib, derived from a de novo combinatorial approach by high-throughput screening and approved by US-FDA in 2007, is the only drug currently available for the treatment of hepatocellular carcinoma. It is a multi-kinase inhibitor, which can prolong the survival rate up to 20%, and the only systemic agent approved to treat advanced, unresectable HCC on the basis of two phase III trials and has been reported to have severe side effects. In the present study, isolated Uttroside B from *Solannum nigrum* and found that Uttroside B is more potent than Sorafenib. These results warrants further clinical evaluation of Uttroside B against liver cancer.

General Study Procedures: Silica gel 60 F254 aluminum TLC plates were used to monitor the reactions with short-wavelength ultraviolet light and by charring the TLC plate after spraying with 15% sulfuric acid to visualize the spots. Column chromatography was performed on silica gel 60-120 and 230-400 mesh. Shimadzu HPLC instrument with C18-phenomenex reverse phase column (250×21.20 mm, 15μ) was used for purification of semi-purified methanolic extract using gradient grade $CH_3OH$ and $H_2O$. $^1H$ and $^{13}C$ NMR spectra were recorded at 500 MHz, 700 MHz and 125 MHz, 176 MHz, respectively. All the spectra were recorded in methanol-d4 and $CDCl_3$. Chemical shifts are given in parts per million and coupling constants in Hz. HRESIMS analysis was performed on a Thermo Scientific Exactive mass spectrometer, with ions given in m/z. *Solanum nigrum* (Linn.) leaf material was dried at room temperature and then grounded to coarse powder resulting in 100 g of the material. The powdered material is subjected to maceration in a shaker incubator at 150 RPM using the gradient solvent system: hexane (500 mL), dichloromethane (500 mL), ethyl acetate (500 mL), and methanol (500 mL), which after filtration and concentration yielded 1.7 g, 2.5 g, 4.2 g, and 6.3 g, respectively. Methanolic extract was found to be most active against liver cancer cell lines.

FIG. 7A is a graph of the cytotoxicity of organic extracts of *S. nigrum* in a panel of five cancer cell lines. The cancer cells were treated with indicated concentrations of hexane extract, dichloromethane extract, ethyl acetate extract and methanol extract, incubated for 72 h as indicated and the cell viability was assessed by MTT assay. FIG. 7B is a graph of the cytotoxicity induced by *S. nigrum* isolated column fractions, in HepG2 cells. HepG2 cells were treated with different concentrations of column fractions as indicated and cell viability was assessed by MTT. Data represent three independent sets of studies. The error bars represent±S.D.

Isolation and purification of Uttroside B (1): The methanolic extract (6.3 g) was subjected to fractionation by column chromatography. The column was packed (silica gel 60-120 mesh, 45 cm×3 cm) with hexane, loaded the compound and eluted using gradient solvent system: hexane/chloroform (500 mL each of 100/0, 80/20, 60/40, 50/50, 40/60, 20/80, 0/100), to chloroform/methanol (500 mL each of 100/0, 95/5, 90/10, 85/15, 80/20, 75/25, 70/30, 60/40, 50/50). Concentration of the fraction eluted during chloroform/methanol (60/40) elution afforded a major polar fraction (1.125 g) which was found to be most active fraction. The polar active fraction (1.125 g) was further subjected to purification by flash column chromatography (silica gel 230-400 mesh, 30 cm×2 cm). The column was packed with chloroform, loaded the compound and eluted using a gradient solvent system: chloroform (100 mL) to chloroform/methanol (300 mL each of 90/10, 80/20, 70/30). Fraction obtained during elution at chloroform/methanol (70/30) was found to contain a pale yellow foamy solid (700 mg), which was found to be a mixture of proline and a saponin as observed in $^1$H-NMR. The mixture of proline and saponin (700 mg) was redissolved in $H_2O$ (6 mL) and then subjected to purification by reverse-phase preparative HPLC, using the following gradient program: solvent A ($H_2O$) and solvent B (MeOH), linear gradient 0 min 0% B, 5 min 10% B, 10 min 20% B, 15 min 30% B (isolated proline, 130 mg, between 10-15 min), 20 min 50% B, 30 min 60% B, 60 min 80% B, 65 min 90% B, 70 min 100% B. The saponin eluted between 65% to 80% B which was monitored by collecting the eluted fractions on a TLC plate and charring with 15% sulfuric acid in ethanol. Concentration followed by lyophilization afforded a white solid Uttroside B (1, 120 mg,).

FIG. 8A is a graph of the dose dependent cytotoxicity induced by mixture of saponin and proline (SP) in HepG2 cells. HepG2 cells were treated with different concentrations of active column fraction and cell viability was assessed by MTT. FIG. 8B is an image of a pale yellow foamy solid, mixture of proline and saponin. The active column mixture isolated from methanolic extract of S. nigrum Linn and this fraction was subjected to vacuum condition. FIG. 8C is a graph of the cytotoxicity of isolated saponin and proline in a dose dependent manner. HepG2 cells were treated with indicated concentrations proline and Uttroside B, incubated for 72 h as indicated and the cell viability was assessed by MTT assay. Data represent three independent sets of studies. The error bars represent±S.D. FIG. 8D is an image of Uttroside B (1) is a white solid. The active compound isolated from active column fraction of methanolic extract of S. nigrum Linn and the pure fraction subjected to vacuum condition.

Figure 9:
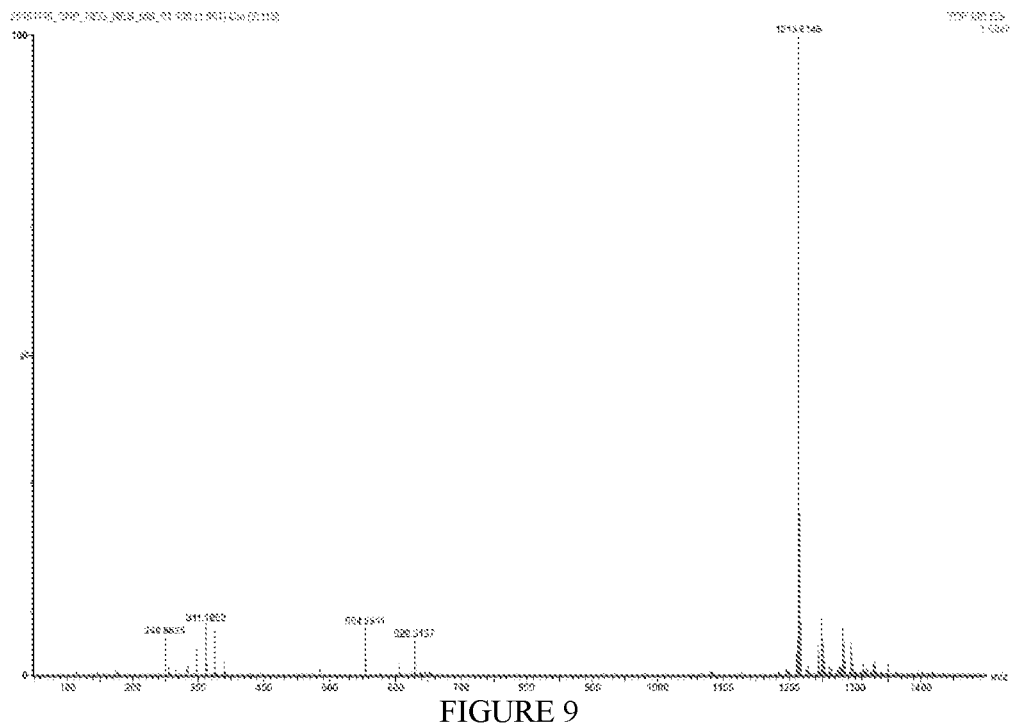
FIG. 9 is an image of a HRESIMS of Uttroside B (1).

FIG. 9 is an image of a HR-ESI-MS of Uttroside B (1).The HR-ESI-MS data of Uttroside B (1) analyzed in negative mode showed (M-H) ion at m/z 1213.6145 indicating a molecular formula $C_{56}H_9O_{28}$. MS-MS negative mode fragmentation afforded ions at ink 1081.5 (M-xyl-H), 919.5 (M-hex-H), 757.4 (M-hex-hex-H). Positive mode fragmentation afforded ions at m/z 1235.5 (M-H$_2$O+K), 1197.5 (M-H$_2$O), 1073.4 (M-H$_2$O-hexose+K), 741.4 (M-H$_2$O-hex-hex-xyl+H), 579.3 (M-H$_2$O-hex-hex-xyl-hex+H), 417.3 (M-H$_2$O-hex-hex-xyl-hex-hex+H), 163.06 (M-hex-hex-xyl-hex-hex-furostanol+H).

Figure 10:
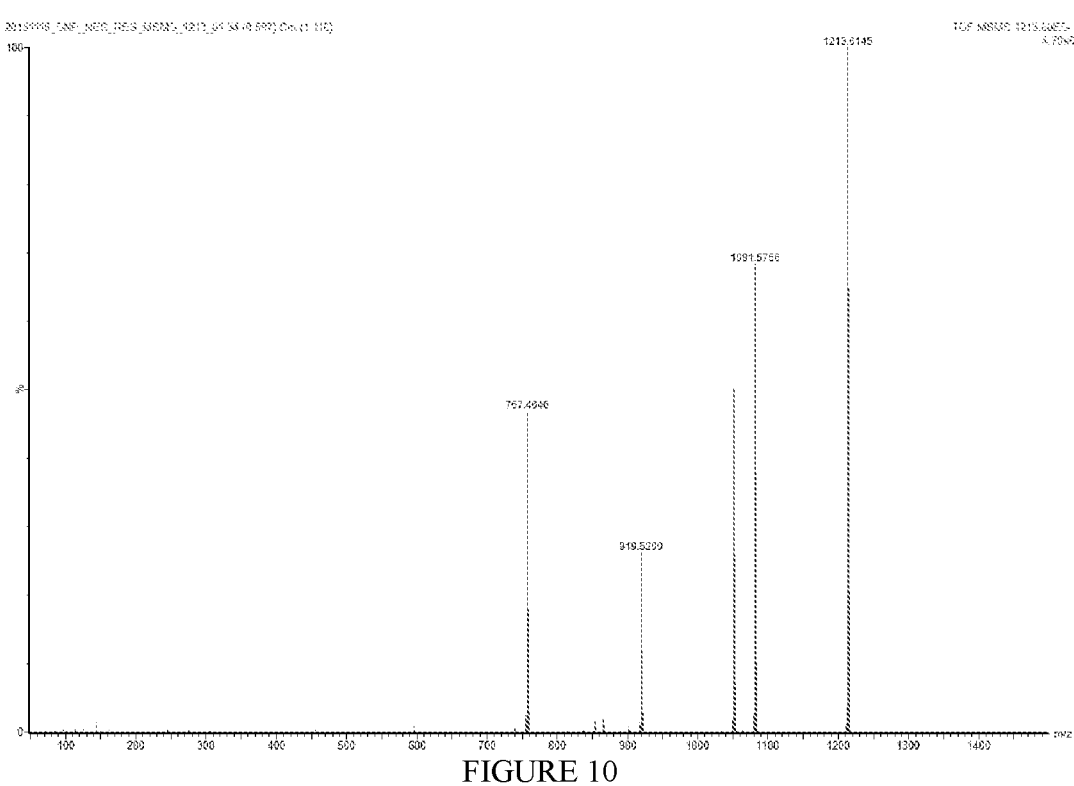
FIG. 10 is an image in negative mode MS-MS analysis of Uttroside B (1).

FIG. 10 is an image in negative mode MS-MS analysis of Uttroside B (1). Key structural characterization: $^1$H and $^{13}$C-NMR studies of Uttroside B was initially performed in CD3OD solvent. The key information pertaining to steroidal furanose ring include H-21 methyl group at $\delta_H$ 40.99 (3H, d, J=7), and hemiketal carbon C-22 at $\delta_C$ 112.5. Owing to complex pattern of signals arising due to sugars in the region between 3 to 4 ppm, Uttroside B was acetylated affording peracetylated compound (2). $^1$H and $^{13}$C-NMR studies of peracetylated compound (2) were performed in CDCl$_3$ solvent. Surprisingly, after acetylation the H-21 methyl group exhibited a downfield shift at $\delta_H$ 1.57 (3H, s), and H-17 at $\delta_H$ 2.45 [1H, d, J=9.8]. In $^{13}$C-NMR, the hemiketal carbon peak disappeared and two additional peaks appeared at $\delta_C$ 103.7 and 151.7 indicating carbons C-20 and C-22, respectively. The aforementioned observations by NMR led us to believe the appearance of a new olefinic bond in the furanose ring due to loss of a water molecule during acetylation.

Figure 11:
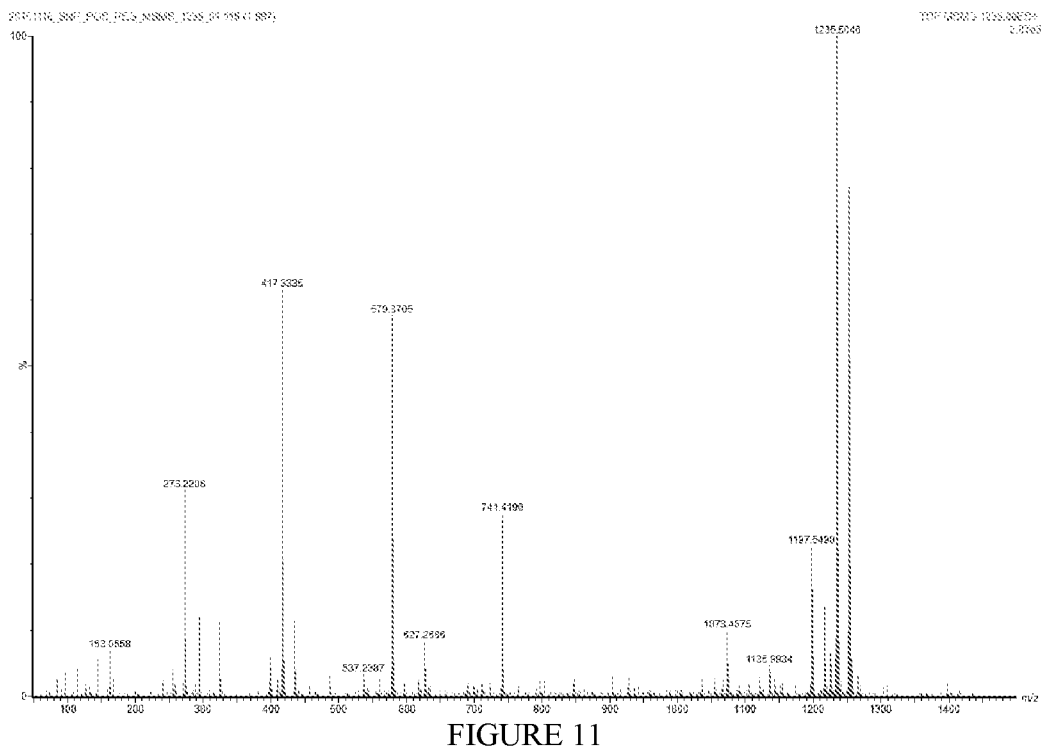
FIG. 11 is an image in positive mode MS-MS analysis of Uttroside B (1).

FIG. 11 is an image in positive mode MS-MS analysis of Uttroside B (1). Peracetylation of Uttroside B (1): Uttroside B (1, 20 mg) was dissolved in 3 mL of pyridine: Ac$_2$O (2:1), and then stirred at room temperature under N$_2$ atmosphere. After 24 h, the reaction mixture was quenched with aqueous saturated NaHCO$_3$ (25 mL), and extracted with ethyl acetate (25 mL×2), dried under Na$_2$SO$_4$ and concentrated. Purification by column chromatography using hexane/ethyl acetate 60/40 to 40/60 afforded the peracetylated compound 2 (10 mg) as a white solid which was characterized by NMR in CDCl$_3$. HR-ESI-MS [M+Na]$^+$ C$_{88}$H$_{124}$O$_{43}$Na of compound 2 calcd for m/z 1891.7414, found 1891.7382.

Figure 12:
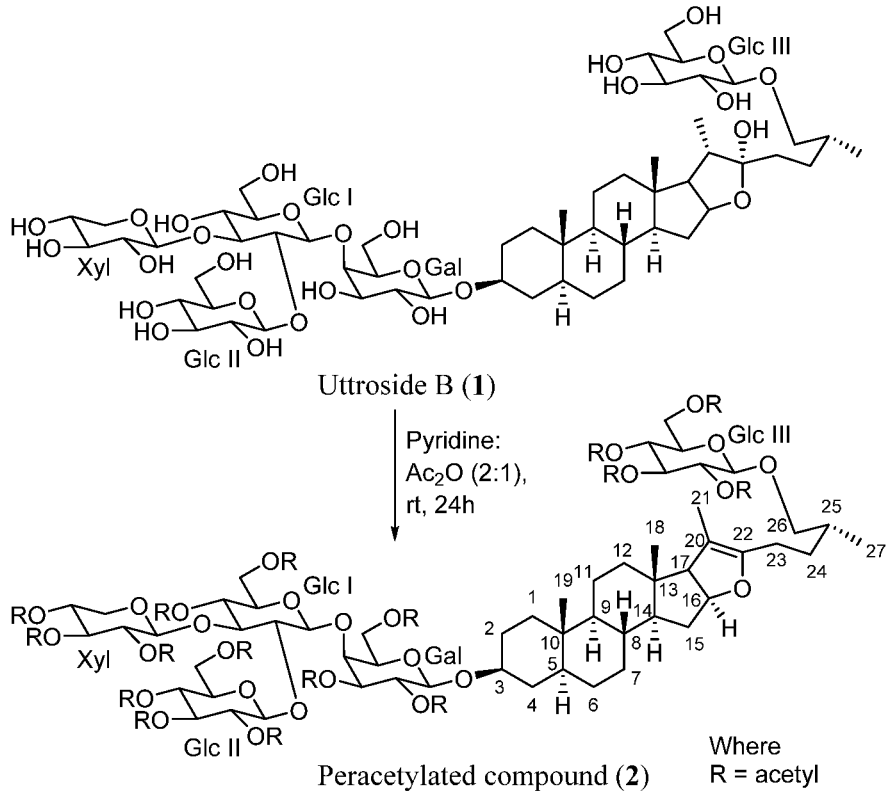
FIG. 12 is an image of the synthesis of peracetylated compound (2) from Uttroside B (1).

FIG. 12 is an image of the synthesis of peracetylated compound (2) from Uttroside B (1). The present invention includes Uttroside B derivative compounds that may include one or more substitutions of the "R" group shown in the peracetylated compound (2). In addition, other derivatives are included through the substitution of the "OR" group entirely. The substitutions may be made to modulate the activity, specificity, solubility or other physical or chemical property. Substitution include but are not limited to aryl, alkylaryl, arylalkoxy, cycloalkyl, bridged cycloalkyl, cycloalkoxy, arylthio, alkylsulfinyl, caboxamido, carbamoyl, arylthio, alkylsulfinyl, caboxamido, carbamoyl, carboxyl, carbonyl, haloalkyl, haloalkoxy, heteroayl, heterocyclic ring, arylheterocyclic ring, heterocyclic compounds, amido, alkylamido carboxylic ester, carboxylic acid, phosphoryl, halogen, or hydrogen.

Figure 13:
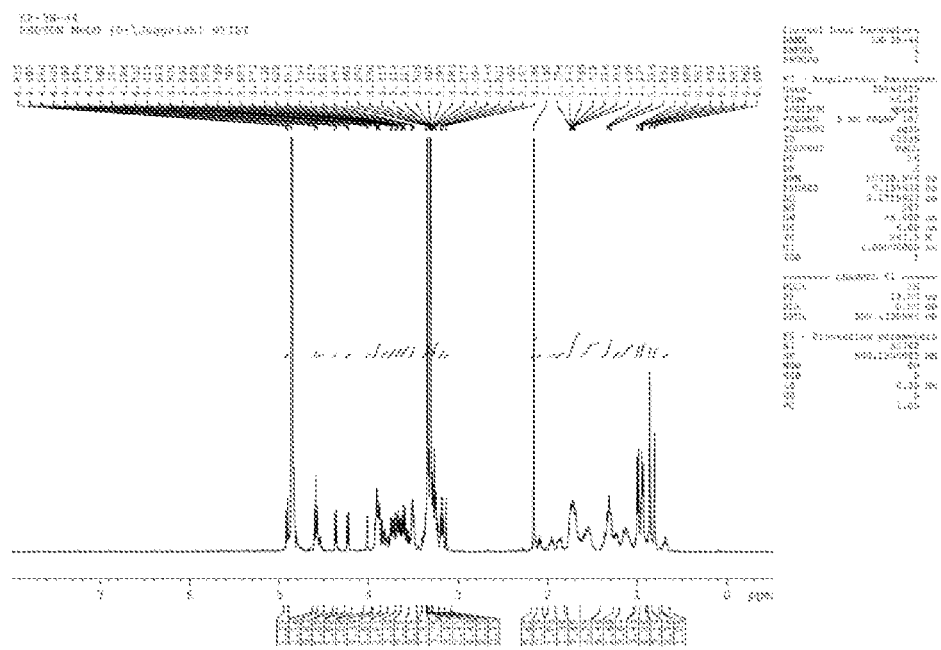
FIG. 13 is an image of the $^1$H NMR spectra of Uttroside B.

FIG. 13 is an image of the $^1$H NMR spectra of Uttroside B.

Figure 14:
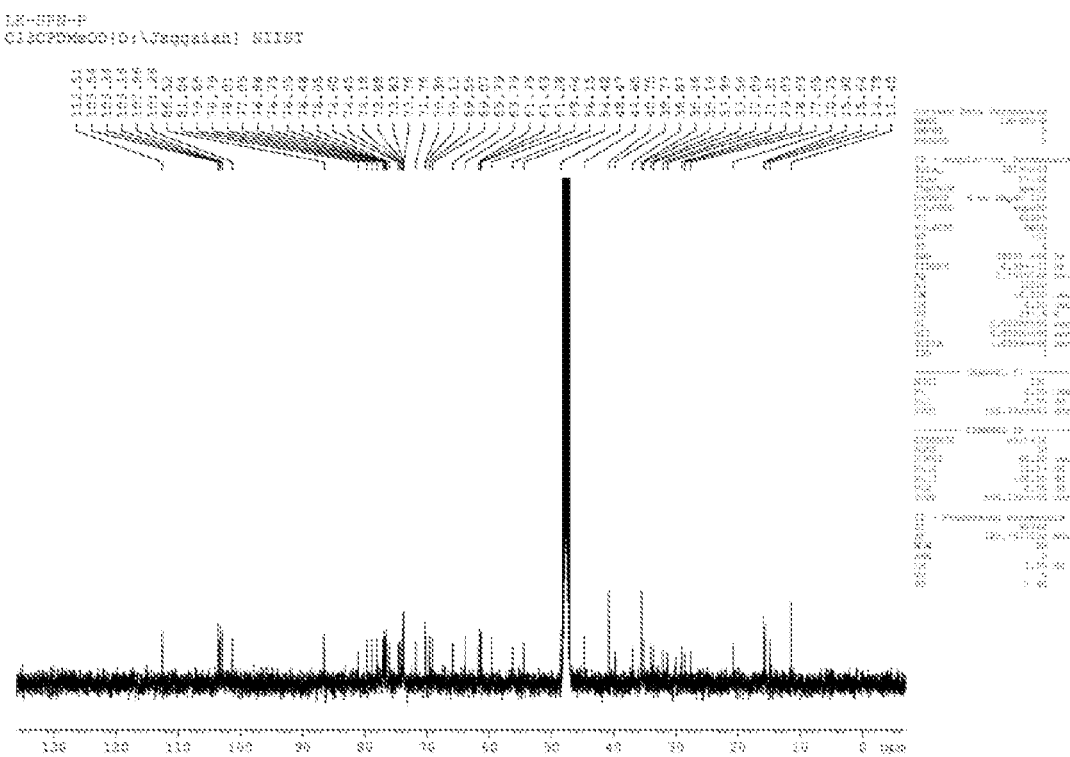
FIG. 14 is an image of the $^{13}$C NMR spectra Uttroside B.

FIG. 14 is an image of the $^{13}$C NMR spectra Uttroside B.

Figure 15:
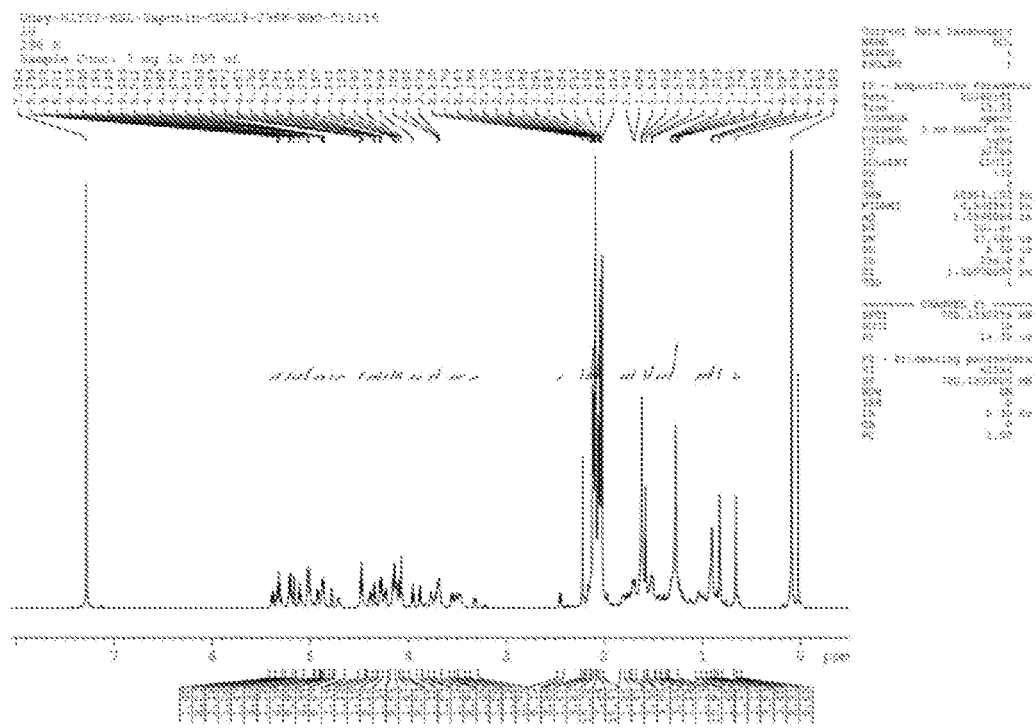
FIG. 15 is an image of the $^1$H NMR spectra of compound 2.

FIG. 15 is an image of the $^1$H NMR spectra of peracetylated compound2.

Figure 16:
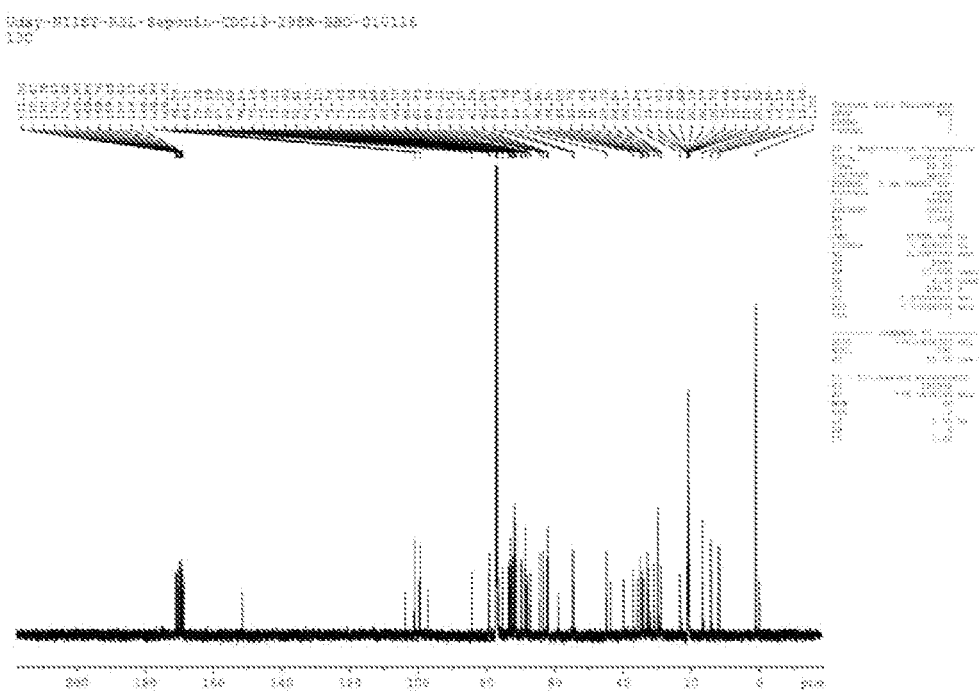
FIG. 16 is an image of the $^{13}$C NMR spectra of compound 2.

FIG. 16 is an image of the $^{13}$C NMR spectra of peracetylated compound2.

Fresh plants were collected in August 2009 from local areas of Thiruvananthapuram, Kerala and were identified by Dr. G. Valsaladevi, Curator, Dept of Botany, University of Kerala, India and a voucher specimen has been deposited at Rajiv Gandhi Centre Biotechnology, Division of Cancer Research laboratory (VOUCHER NO: CRP 05).

The cervical cancer cell line (HeLa), the breast cancer cell line (MDA-MB-231), the lung cancer cell lines (A549), the colon cancer cell line (HCT-116), the skin cancer cell line (A375), liver cancer cell lines (HepG2, SK-Hep-1, Hep3B and Huh-7) leukemia cell line (HL60) and normal hepatocytes (Chang Liver) were procured from National Centre for Cell Sciences (Pune, India)

Important cell culture reagents such as Dulbecco's Modified Eagle Medium (DMEM) and streptomycin sulphate were obtained from Invitrogen Corporation (Grand Island, USA). SUPERSENSITIVE™ Polymer-HRP IHC Detection System Kit was obtained from Biogenex Laboratories Inc (San Ramon, USA) and was used for immunohistochemistry studies. MTT reagent and AmershamECL PLUS™ Western blotting reagents were purchased from GE Healthcare Life Sciences (Piscataway, USA). Antibodies against Caspases, β-actin, p-p42/44, p-JNK, p-p38, p-Akt, p-mTOR and Vinculin were obtained from Cell Signaling Technologies (Beverly, Mass., USA) and the antibody against PARP was purchased from Santa Cruz Biotechnology (Santa Cruz, Calif., USA). All the chemicals used for extraction, column chromatography and high performance liquid chromatography (HPLC) were of analytical grade and were obtained from Merck Ltd, Mumbai, India. Silica gel (60-120 & 230-400 mesh) used for column chromatography and pre-coated silica gel 60 GF254 plates used for thin-layer chromatography (TLC) were from Merck Ltd, Germany. All other chemicals were purchased from Sigma Chemicals (St. Louis, Mo., USA) unless otherwise mentioned.

Stocks of crude extracts and isolated compound of S. nigrum was prepared in DMSO for the in vitro studies and stored at −20° C. The DMSO concentration in all studies, including controls, was ≤0.2%. Cell viability assay was performed after 72 h of drug treatment while whole cell lysate preparation and cell cycle analysis were done after 24 h and 48 h of drug treatment. For studying NF-κB and AP-1, Uttroside B was incubated for 2 h before extraction.

MTT [3-(4,5-dimethylthiazole-2-yl)-2,5-diphenyltetrazolium bromide] assay is a standard colorimetric assay, suitable for analyzing proliferation, viability, and cytotoxicity.

Briefly, the HepG2 cells were seeded in 96-well plates (2000 cells/well). After overnight incubation, cells were treated with different concentrations of organic extracts (25-250 μg/ml) of *S. nigrum* and the isolated compound Uttroside B (250-1250 nM) for 72 h and cytotoxicity was measured. Fresh media containing 25 μL of MTT solution (5 mg/mL in PBS) and 75 μL of complete medium was added to the wells and incubated for 2 h. At the end of incubation, lysis buffer (20% sodium dodecyl sulphate in 50% dimethyl formamide) was added to the wells (0.1 mL/well) and incubated for another 1 h at 37° C. At the end of incubation, the optical density was measured at 570 nm using ELISA plate reader (Bio-Rad). The relative cell viability in percentage was calculated as ($A_{570}$ of treated samples/$A_{570}$ of untreated samples)×100. The IC50 values were extrapolated from polynomial regression analysis of study data.[17]

The clonogenic cell survival assay determines the ability of a cell to proliferate indefinitely, thereby retaining its reproductive ability to form a large colony or a clone.[5] This technique is used to determine the long-term fate of proliferating cells, because it is difficult to identify an irreversible arrest of cell growth that occur late using other detection methods.[6] Briefly, 500-1000 cells/well were seeded in 6 well plates and were treated with different concentrations of isolated compounds (Uttroside B) for 72 h. Then the media was aspirated and fresh media was added and incubated for 1 week. The clones developed were fixed with glutaraldehyde and stained using crystal violet. The clones were then viewed under microscope, photographed and the colonies were counted and graph was plotted.[16]

Western blot analysis. Approximately $0.5 \times 10^6$ cells were grown on 60 mm culture plates and exposed to drugs as indicated for the desired time. The cells were then scraped out, washed in ice cold 1× PBS and pelleted down at 13000 rpm for 2 min. The pelleted cells were suspended in 150 μL of ice-cold whole cell lysis buffer[(20 mMTris of pH 7.4, 250 mM NaCl, 2 mM EDTA, 0.1% Triton, 1 mM DTT (1,4-dithiothreitol), 0.5 mM PMSF, 4 mM sodium orthovanadate, aprotinin (5 mg m/L) and leupeptin (5 mg m/L)] and kept in ice for 30 min, with intermittent vortexing every 5 min. After incubation, the lysate was centrifuged at 13000 rpm for 10 min at 4° C. and the supernatant was collected. The total protein content in the lysate was estimated by Bradford's method, and was then denatured by boiling with 5× loading dye before separating the proteins by SDSpolyacrylamidegel electrophoresis (SDS-PAGE). Following electrophoresis, the polyacrylamide gel and a PVDF membrane were equilibrated with Towbins buffer (1 L, 25 mM Tris, 192 mM glycine, 20% (v/v) methanol (pH 8.3) for 15-30 min and the separated proteins were electro-transferred to PVDF membrane (Hybond-P, GE Healthcare Life science) using Bio-Rad Mini PROTEAN III wet blot apparatus at 100 V for 2 h at cold conditions. After the transfer, the membrane was rinsed with TBS-T (20 mM Tris pH 7.5, 150 mM NaCl, 0.1% Tween 20) buffer and stained with Ponceau-S to ensure uniform transfer. After washing off the Ponceau stain with TBST, the membrane was exposed to 5% fat free milk in TBST buffer for 1 h at room temperature to block the nonspecific binding of antibodies, followed by overnight incubation with the primary antibody [1:1000 dilution] in 3% BSA in TBST buffer at 4° C. Excess antibody was washed off with TBST buffer and incubated with corresponding secondary antibody [1:5000 dilution] coupled with horse radish peroxidase (HRP) in 5% fat free milk in TBST buffer. The bands were visualized using enhanced chemiluminescence kit (Millipore, St Charles, Mo., United States) following manufacturer's protocol.

Flow cytometry: Cell cycle analysis helps in distinguishing the distribution of a population of cells to the different stages of the cycle. Cell cycle analysis using flow cytometry was performed to investigate the cell cycle arrest induced by Uttroside B. Cell cycle analysis is performed by quantitative measurement of nuclear DNA content in a cell by staining DNA with propidium iodide. Propidium iodide is a DNA binding dye which intercalates into the major groove of double-stranded DNA and its excitation and emission peaks observed at 488 nm and around 600 nm. When propidium iodide is added to a suspension of penneabilized cells, its incorporation will be proportional to the DNA content and the stage of cell cycle can be determined by measuring total fluorescence emission using a flow cytometer. Briefly, $0.5 \times 10^6$ cells were seeded in 60 mm plates and subjected to Uttroside B treatment for 48 h followed by trypsinization and pellet down. Curcumin (25 μM, 24 h) was used as the positive control. The cell pellets were fixed in 70% ice-cold ethanol, treated with 5 μL (10 mg/mL) RNase A and incubated for 30 min at 37° C., 10 μL (10 mg/mL) propidium iodide was added and filtered via filter tubes and analyzed using the FACS Aria™ flow cytometer (BD Biosciences).

Radiolabeling of oligonucleotide probes for electrophoretic mobility shift assay:HepG2 Cells were treated with Uttroside B for two hours, scraped and suspended in 150 μL of lysis buffer (10 mM HEPES(pH 7.9), 10 mM KCl, 0.1 mM EDTA, 0.1 mM EGTA, 1 mM DTT, 0.5 mMphenylmethylsulfonyl fluoride, 2 μg/mL leupeptin, 2 μg/mL aprotinin, 0.5 mg/ml benzamidine) for 30 min, after which 4.5 μl of 10% Nonidet P-40 was added. The pellet was suspended in 25 μL of nuclear extraction buffer (20 mM HEPES, pH 7.9, 0.4 M NaCl, 1 mM EDTA, 1 mM EGTA, 1 mM DTT, 1 mM phenylmethylsulfonyl fluoride, 2 μg/mL leupeptin, 2 μg/mL aprotinin, 0.5 mg/mL benzamidine) centrifuged after 2 h and the nuclear extract collected (8 μg of protein) was used to perform EMSA by incubating it with 16 fmol of 32P end labeled 45-mer double stranded NF-κB oligonucleotide from the human immunodeficiency virus-1 long terminal repeat SEQ ID No: 1(5-TTGTTA-CAAGGGACTTTCCGCTGGGGACTTTCCAGG-GAGGCGTGG-3) and 1 μg/ml poly(dIdC) in a binding buffer (25 mM HEPES (pH 7.9), 50 mM NaCl, 0.5 mM EDTA, 0.5 mM DTT, 1% Nonidet P-40, and 5% glycerol) for 30 min at 37° C. The DNA-protein complex was resolved using a 6.6% native polyacrylamide gel and the radioactive bands were visualized by phosphorimaging (Bio-Rad Personal FX).[17]

Toxicological evaluation:a. Animals: Six to eight-week-old female Swiss albino mice (18-22 g) were obtained from the Animal Research Facility of Rajiv Gandhi Centre for Biotechnology and the study was performed under protocols approved by Institutional Animal Ethical Committee of Rajiv Gandhi Centre for Biotechnology (IAEC No: 151 (a)/RUBY/2012) b. Acute toxicity study: Swiss albino mice were randomly divided into 3 groups of 6 animals each and were allowed to acclimatize for a week. Group I was taken as the control, which received only vehicle, while Group II and III received a single dose of Uttroside B dissolved in PBS (10 mg/kg and 50 mg/Kg body weight respectively). The mice were observed continuously for 1 h, for any gross behavioral changes and death, and then intermittently for the next 6 h and 24 h. The animals were observed frequently for the next 7 days from the day of treatment after which, the animals were euthanized in a $CO_2$ chamber. The blood serum was collected for analyzing biochemical parameters of liver function, the abnormal values of which are indicative of toxicity. The liver was fixed in 10% buffered formalin and the thin cryostat sections (LEICA CM 1850UV Cryostat) were stained with haematoxylin and eosin for histopathological evaluation.[17]

Swiss albino mice were randomly divided into 2 groups of 6 animals each and were allowed to acclimatize for a week. Group I received vehicle and Group II received 10 mg/Kg body weight of Uttroside B. The compounds were given as intraperitonial injection on alternate days, thrice in a week, for 3 months. The animals were observed frequently during this period after which, the animals were euthanized in a $CO_2$ chamber. The blood serum was collected for analyzing biochemical parameters of liver function, the abnormal values of which are indicative of hepatotoxicity. The liver was fixed in 10% buffered formalin and the thin cryostat sections were stained with haematoxylin and eosin for histopathological evaluation.[9]

In vivoHepG2-Xenograft model: All animal studies were performed in accordance with the protocols approved by Institute Animal Ethical Committee IAEC No: 151(b)/RUBY/2012. An ectopic xenograft model in NOD-SCID (NOD.CB17-Prkdcscid/J) mice was used for evaluating the anti-cancer properties of Uttroside B. The animals required for this study were obtained from Animal Research Facility of Rajiv Gandhi Centre for Biotechnology and were fed with standard food pellets and autoclaved water ad libitum. Animal handling, tumor induction, drug treatment and tissue collection were performed in sterile conditions.

Evaluation of the anticancer activity of Uttroside B, isolated from *S. nigrum* in human liver cancer (HepG2)-xenograft model: xenografts models were established in NOD-SCID mice as described in literature.[10] Male NOD-SCID (NOD.CB17-Prkdc$^{scid/J}$) mice of age 6-8 weeks were used for the study. Tumors were induced by subcutaneous injection of HepG2 cells ($7 \times 10^6$ cells in 100 µL matrigel) in the lower right or left flank of mice and were allowed to grow for a period of two weeks to attain a size of approximately 50-100 mm$^3$ as measured by Vernier calipers. The mice were then randomly grouped into control and treatment group of 9 animals each. The treatment groups were injected intraperitoneally with Uttroside B (10 mg/kg doses thrice weekly) for one month. Tumor volume was measured every seven days to evaluate tumor growth and drug response. The animals were sacrificed at the end of the study and tumor samples were collected for histopathological and immunohistochemical analysis.

Histopathology: The tissue cryo-sections were washed with PBS (5 min, 2 times) and distilled water for 5 min. Then the sections were stained with hematoxylin for 2 min. Excess stain was washed off and the slides were dipped in differentiation solution for 1-2 s. They were then kept in tap water for 10 min and 70% Isopropyl alcohol for 5 min respectively and were counter stained with eosin solution for 1 min. The sections were then transferred to 100% Isopropyl alcohol and kept for 2 min, cleared in xylene for 1 h and were mounted using DPX. Stained sections were observed using a light microscope and were photographed. The pathology of liver and tumor tissue sections were examined and verified by Dr. Sankar Sundaram, Professor of Pathology, Medical College, Thiruvananthapuram.

Immunohistochemistry of xenograft tissue sections: Immunohistochemical analysis of various proteins in the xenograft tumor tissue sections was performed using the detection kit, as per manufacturer's protocol Super Sensitive™ Polymer-HRP IHC Detection System (Biogenex, Calif., USA). Paraformaldehyde-fixed OCT-embedded tissue sections were kept in PBS for 15 min. Antigen retrieval was done using heat-induced antigen retrieval method using citrate buffer. Nonspecific antibody binding sites on tissue sections were blocked by Power Block™ Reagent supplied with the kit. The pre-diluted primary antibody was added enough to cover the sections and were incubated for 12 h at 4° C. The slides were washed off with PBS to remove unbound primary antibody. The sections were then covered with Super Enhancer™ Reagent, incubated for 20 min at room temperature, in order to enhance the signal and rinsed with PBS. Sections were then incubated with Poly-HRP Reagent for 30 min at room temperature. They were then washed using PBS after which, substrate solution (DAB chromogen) was added and incubated for 5 min. Sections were then washed in PBS and counterstained using Mayer's hematoxylin for 1 min and the sections were mounted using DPX. Images were captured using a Leica DM 1000 microscope at 40×.

Acridine Orange Staining for Acidic Vesicular Organelles (AVOs)

The presence of acidic vesicles, which are characteristics of autophagosome can be analyzed using this method. Acridine orange stains the nucleus green and the acidic vesicular organellae (AVOs) as red.[32] To detect the presence of AVOs in HepG2 cells, $5 \times 10^3$ were seeded in 96 well plates, and treated with Uttroside B and incubated for 24 h. The cells were rinsed with 1× PBS twice. The treated cells were then stained with acridine orange, which was added at a final concentration of 1 µg/mL and incubated for 15 min and immediately photographed using a fluorescent microscope.

Isolation of Plasmid and Transfection

The development of a new vector called ptf-LC3B leading to the expression of a double-tagged GFP-RFP-LC3B protein has helped in the study of autophagy flux and this recombinant protein allows to distinguish between autophagosomes (in yellow) and autophagolysosomes (in red).[33] The pGFP-mRFP-LC3B (ptf-LC3) vector was purchased from Addgene (21074). Briefly, plasmid present in the bacterial pellet was isolated according to manufacturer's instruction (GenElute™ Plasmid Miniprep Kit-Sigma-Aldrich). HepG2 cells were transfected transiently with tandem repeats of GFP-RFP tagged LC3 (ptfLC3) using the Lipofectamine LTX and Plus Reagent Kit (Invitrogen, USA) according to manufacturer's protocol. Briefly, PtfLC3 vector Opti-MEM transfection medium (Solution A) was mixed with Lipofectamine reagent dissolved in Opti-MEM transfection medium (Solution B) and incubated for 45 min at room temperature. The transfection mixture was then overlaid into the cells in a six well tissue culture plate at 50-80% density and incubated for 6 hours. The medium with the transfection mixture was aspired after 24 h.

Immunofluorescence

For immunocytochemical localization of intracellular proteins, the cells were grown on glass coverslips and exposed to Uttroside B for 24 h. The cells were then washed with PBS, fixed with 4% paraformaldehyde, permeabilized with 0.1% Triton X-100 for 15 min at room temperature and blocked with 3% BSA in PBS for 1 h. Antibody (anti-LC3) (1:100) diluted in PBS containing 1% BSA were added to cover the cells and incubated overnight at 4° C. Unbound antibodies were washed off with PBS and the cells were incubated with 2 µg/ml Fluorescein-conjugated or Rhodamine-conjugated secondary antibodies for 1 h at room temperature. The unbound secondary antibodies were then washed off and the nuclei of the cells were stained with 0.5 µg/ml 4′,6-diamidino-2-phenylindole (DAPI) for 10 min. The coverslips with cells were mounted in glycerol, examined and photographed using a fluorescence microscope.

Beclin siRNA Transfection

HepG2 was transiently transfected with Beclin siRNA and control siRNA using Lipofectamine LTX Plus reagent kit according to manufacturer's protocol (Invitrogen, USA). $0.35 \times 10^6$ cells per well were seeded in a six well tissue culture plate containing 2 ml antibiotic-free normal growth medium supplemented with FBS and the cells were incubated to attain 60% confluency. Beclin siRNA duplex solution (Solution A) was added directly to the dilute transfection reagent (LP LTX plus reagent) (Solution B). The solution was mixed gently by pipetting up and down and incubated for 45 minutes at room temperature. The cells were washed gently with 2 ml of transfection medium (optiMEM medium). For each transfection, 0.8 ml transfection medium was added to each tube containing the siRNA transfection reagent mixture (Solution A+Solution B). It was mixed gently and the mixture was overlaid onto the washed cells. The cells were incubated for 5-7 h at 37° C. in a $CO_2$ incubator. 1 ml of normal growth medium was added after removing the transfection medium and the cells were incubated for an additional 18-24 h. The silencing of Beclin expression was confirmed by Western blotting with anti-beclin-1 and the transfection efficiency was standardized at 50-60 h before the drug treatment.

Figure 17:
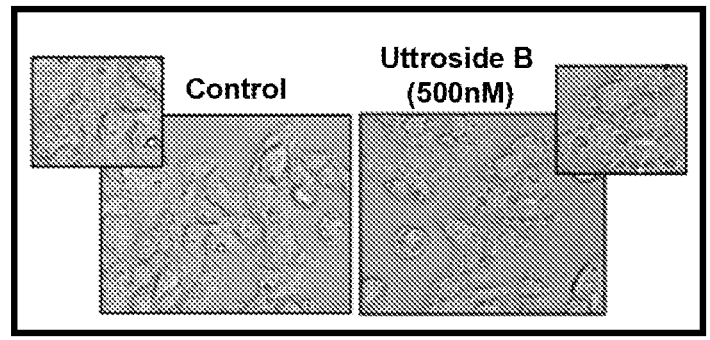
FIG. 17 is a representative image showing the morphological changes and vacuole formation induced by Uttroside B in HepG2 cells.

FIG. 17 is a representative image showing the morphological changes and vacuole fomiation induced by Uttroside B in HepG2 cells. HepG2 cells were treated with Uttroside B as indicated, incubated for 24 h and HepG2 cells were studied for their morphological changes after treatment with Uttroside B, by Phase contrast microscopy. Uttroside B also induces vacuole formation, a characteristic feature of autophagy.

Figure 18:
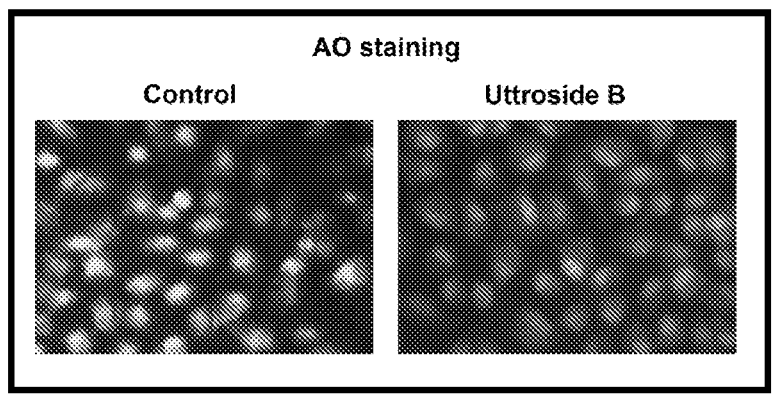
FIG. 18 is a representative image showing that Uttroside B induces acidic vacuole formation in HepG2 cells by Acridine orange staining.

FIG. 18 is a representative image showing that Uttroside B induces acidic vacuole formation in HepG2 cells by Acridine orange staining. To further confirm the autophagic induction by Uttroside B in HepG2 cells, the cells were exposed to cytotoxic concentration of Uttroside B for a period of 24 h and stained with Acridine orange dye. AO orange stains nucleus green and acidic vesicular organelle, mainly autophagosome, bright red. It crosses into acidic compartments and becomes protonated. The protonated dye stacks and stacked acridine orange emits in the red range. AO positivity, a preliminary indication of increased autophagosomes was clearly visible in Uttroside B-treated HepG2 cells.

Figure 19:
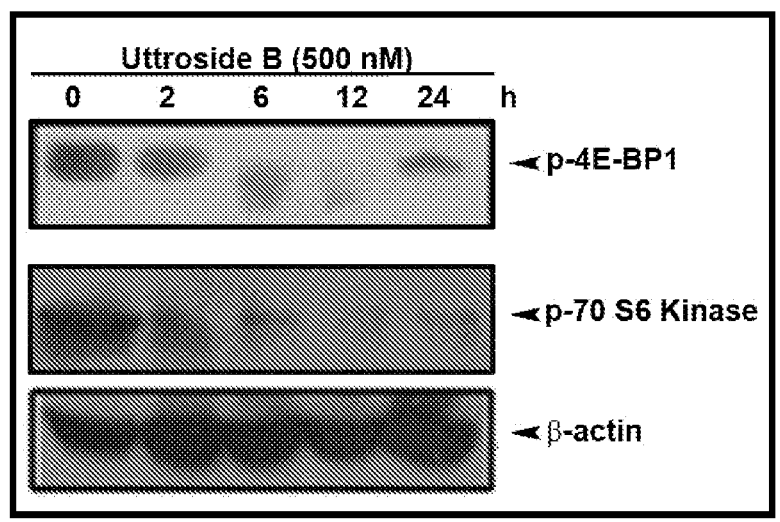
FIG. 19 shows the Western blot image showing the kinetics of Uttroside B-induced phosphorylation of mTOR downstream targets, phospho-4E-BP1 and phospho-p70S6 Kinase.

Uttroside B inhibits mTOR signaling, a crucial survival signal in liver cancer. FIG. 19 shows the Western blot image showing the kinetics of Uttroside B-induced phosphorylation of mTOR downstream targets, phospho-4E-BP1 and phospho-p70S6 Kinase. HepG2 cells were treated with Uttroside B at different time intervals and the whole cell lysate was resolved on a 15% gel and immunoblotted against phospho-4EBP1 and phospho-p70S6 Kinase antibodies. Concomitantly, the phosphorylation of p70S6 kinase and 4E-BP-1, two m-TOR substrates whose phosphorylation can be considered as the read out of m-TOR activity, was found reduced in response to Uttroside B-treatment. Uttroside B inhibits mTOR signaling, a crucial survival signal in liver cancer. mTOR plays a pivotal role in cell growth and metabolism of HCC and are up-regulated in 40-50% of HCC. Moreover, an up-regulation is frequently observed in cholangiocarcinoma, the second most common primary cancer of the liver[31]. Uttroside B-treatment has also been shown to inhibit the phosphorylation m-TOR at 2448 and 2481 phosphorylation sites [see FIG. 4E].

Figure 20:
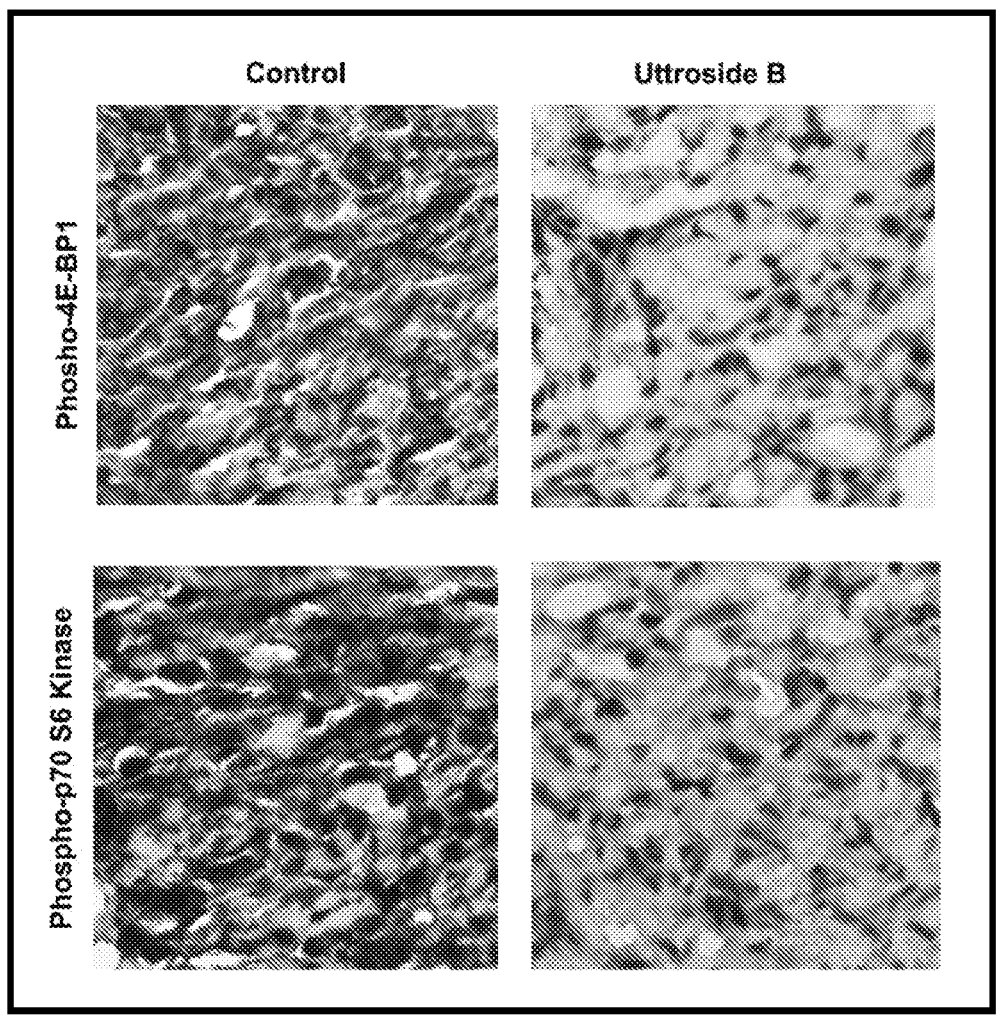
FIG. 20 shows the representative H&E image indicating that Uttroside B significantly down-regulates the expression of phospho-4EBP1 and phospho-p70S6 Kinase in HepG2 xenograft tumors in NOD-SCID mice.

FIG. 20 shows the representative H&E image indicating that Uttroside B significantly down-regulates the expression of phospho-4EBP1 and phospho-p70S6 Kinase in HepG2 xenograft tumors in NOD-SCID mice. Immunohistochemical staining of the control and Uttroside B-treated tumor tissue was performed. The tissue collected from NOD-SCID mice xenograft study was also checked for the phosphorylation status of the p70S6K and 4E-BP-1. As observed in the in vitro study, a significant down-regulation in the phosphorylation status of both these molecules were observed in the tissues too.

Figure 21:
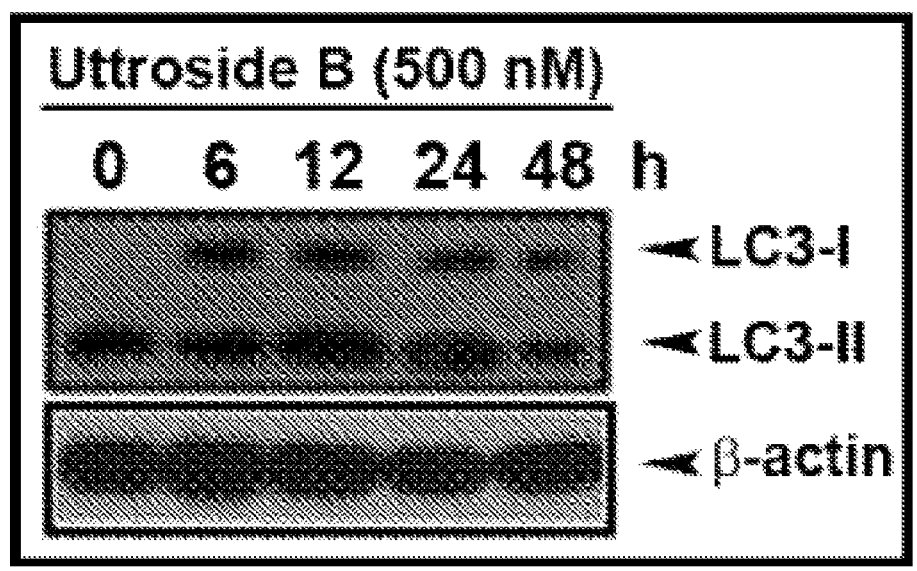
FIG. 21 shows the time dependent effect of Uttroside B on the endogenous conversion of LC3I to LC3II (microtubule-associated protein 1 light chain 3) in HepG2 cells.

Uttroside B induces autophagy in HepG2 cells. FIG. 21 shows the time dependent effect of Uttroside B on the endogenous conversion of LC3I to LC3II (microtubule-associated protein 1 light chain 3) in HepG2 cells. Cells were treated with Uttroside B at different time intervals and the whole cell lysate was resolved on a 15% gel and immunoblotted against LC3 antibody. The compounds that mediate its activity by blocking mTOR signaling axis may probably induce autophagy since there are signaling routes which suppress autophagy through mTOR activity. Nevertheless, it can significantly influence the cell death induced by anti-tumor agents and it is essential to investigate the status of autophagy process in response to Uttroside B-treatment and to analyze its role in regulating the dynamics of cell death. LC3 expression, the conversion of microtubule associated protein light chain 3 (LC3)-I to LC3-II, an autophagosome marker is a classical marker of autophagy.[32,34,35] Autophagy is a dynamic process that could degrade autophagosome membrane protein LC3II along with cellular cargo loaded in autophagosome. Hence, autophagy is more accurately represented by gauging the turnover rate of LC3II rather than representing its expression level at a given instance.

Figure 22:
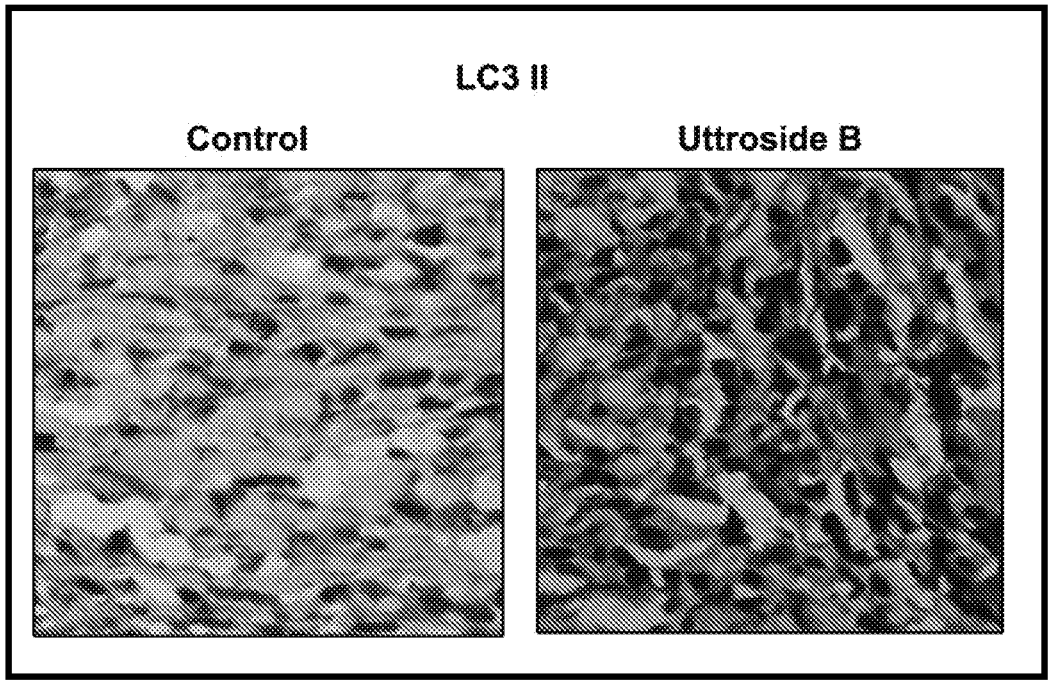
FIG. 22 shows the H&E staining of tumor sections of Uttroside B treated NOD-SCID mice carrying HepG2 xenografts showing significant down-regulation of LC3.
Figure 23:
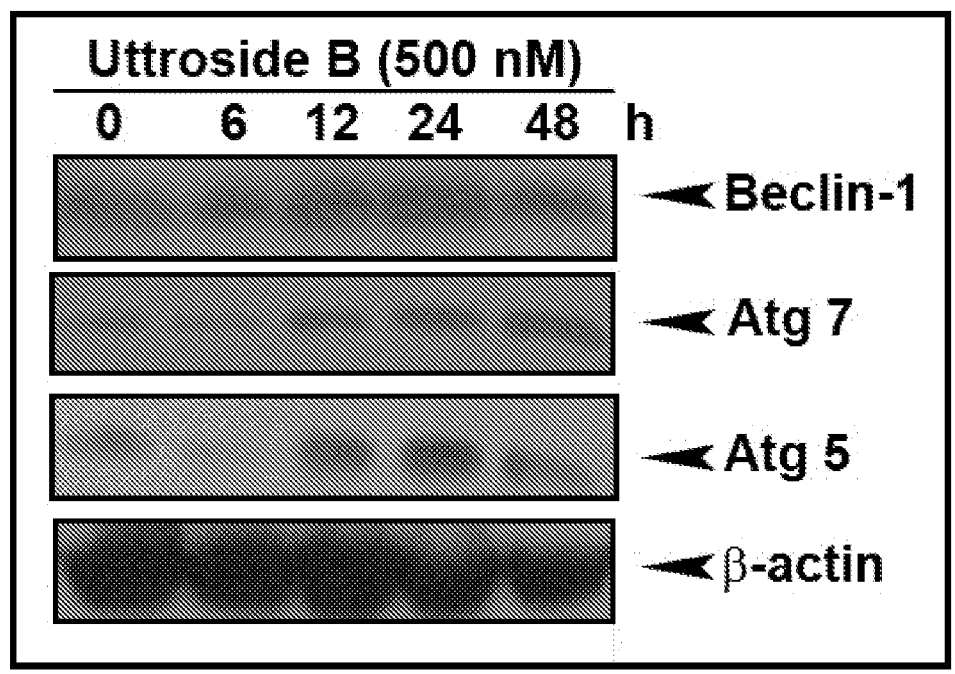
FIG. 23 shows the time-dependent effect of different autophagy related proteins beclin-1, Atg 7, Atg 5 in HepG2 cells.
Figure 24:
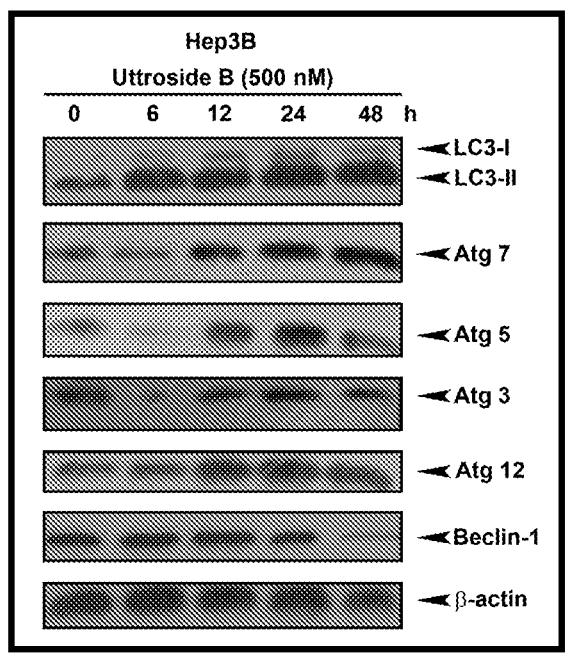
FIG. 24 shows the time dependent effect of Uttroside B on different autophagy related proteins Beclin-1, Atg 7, Atg 5, Atg 3, Atg 12 in another liver cancer cell, Hcp3B cells.
Figure 25:
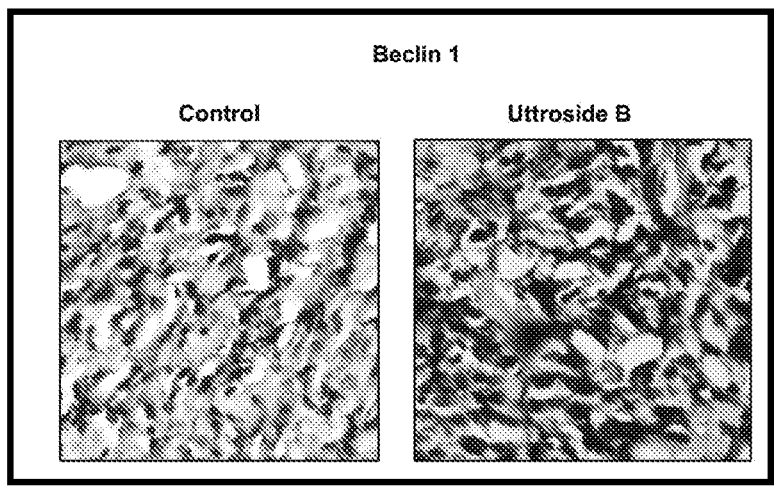
FIG. 25 shows that Uttroside B significantly up-regulates the expression of beclin-1 in HepG2 xenografts in NOD-SCID mice.

FIG. 22 shows the H&E staining of tumor sections of Uttroside B treated NOD-SCID mice carrying HepG2 xenografts showing significant down-regulation of LC3. Immunohistochemical staining of the control and Uttroside B-treated tumor tissue was performed using LC3 antibody. For checking whether Uttroside Bcan have the same effect in liver tumors, IHC analysis was performed in both control and Uttroside B-treated tumor sections. The tissue level expression status of LC3 was also very high in Uttroside B-treated mice. FIG. 23 shows the time-dependent effect of different autophagy related proteins beclin-1, Atg 7, Atg 5 in HepG2 cells. Cells were treated with Uttroside B at different time intervals and the whole cell lysate was resolved on a 15% gel and immunoblotted against LC3, Beclin-1, Atg 7 and Atg 5 antibodies. To study the expression status of different autophagy related proteins in HepG2 and Hep3B, cells were treated with Uttroside B in a time dependent manner and immunoblotted against beclin-1, Atg 5, Atg 3, Atg 12. Results indicate that Uttroside B induces up-regulation of all autophagy related proteins in a time dependent manner in HepG2. FIG. 24 shows the time dependent effect of Uttroside B on different autophagy related proteins Beclin-1, Atg 7, Atg 5, Atg 3, Atg 12 in another liver cancer cell, Hep3B cells. Cells were treated with Uttroside B at different time intervals and the whole cell lysate was resolved on a 15% gel and immunoblotted against Beclin-1, Atg 7, Atg 5, Atg 3 and Atg 12 antibodies. Similarly, Uttroside B also induced Atg5, Atg7 and LC3 in a time dependent manner in Hep3B cells too. FIG. 25 shows that Uttroside B significantly up-regulates the expression of beclin-1 in HepG2 xenografts in NOD-SCID mice. Immunohistochemical staining of the control and Uttroside B-treated tumor tissue was performed using Beclin-1 antibody. Beclin is an important protein present in a complex, which helps in the biogenesis of autophagosome.[36] To evaluate the expression status of beclin-1 in tumor sections of human liver cancer xenografts, immunohistochemical analysis was conducted. The tissue level expression status of beclin-1 was also very high in Uttroside B-treated mice illustrating its efficacy in inducing autophagy in liver cancer cells.

Figure 26:
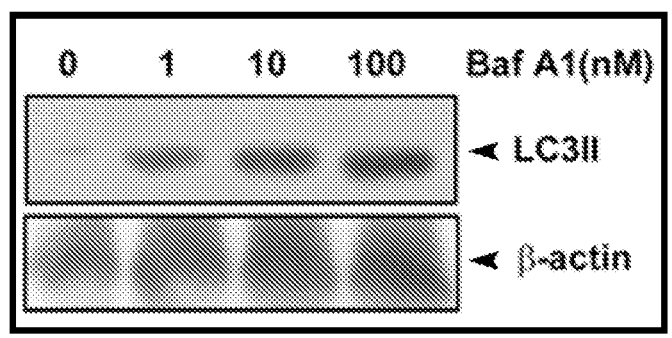
FIG. 26 shows the standardization of concentration of Bafilomycin Al for saturating autophagosome-lysosome blockade.

FIG. 26 shows the standardization of concentration of Bafilomycin Al for saturating autophagosome-lysosome blockade. Concentration dependent effect of BafilomycinAl on the endogenous conversion of LC3I to LC3II in HepG2 cells. Cells were treated with Bafilomycin Al at different concentration and the whole cell lysate was resolved on a 15% gel and immunoblotted against LC3 antibody. Uttroside B is an autophagy inducer in HepG2 cells as analysed by autophagy flux using Bafilomycin Al. It was already discussed previously that an increase in the lipidated and autophagosome associated form of LC3 (LC3II), one of the hall mark of autophagosome induction, was observed in both Uttroside B-treated HepG2 and Hep3B cell lines. The increase in LC3 II could not be considered as a fool proof of autophagic induction because a blockage in any step leading from autophagosome maturation to its fusion with lysosomes could cause its accumulation. So, the effect of Uttroside B in HepG2 cells were analyzed for autophagy flux, a more accurate read out of autophagy on co-treatment with Bafilomycin, an autophagy-lysosome inhibitor. Bafilomycin A, blocks autophagy by blocking the fusion of autophagosome with lysosome which cause the accumulation of autophagosome or LC3. First, the concentration of Bafilomycin Al required for saturating the blockage of autophagy-lysosome fusion was standardized. The efficacy of Bafilomycin Al, in terms of blocking autophagosome degradation in HepG2, was found peaked at 10 nM, beyond which no further accumulation of LC3 II was noted, which matched with the earlier reports.[32,37,38]

Figure 27:
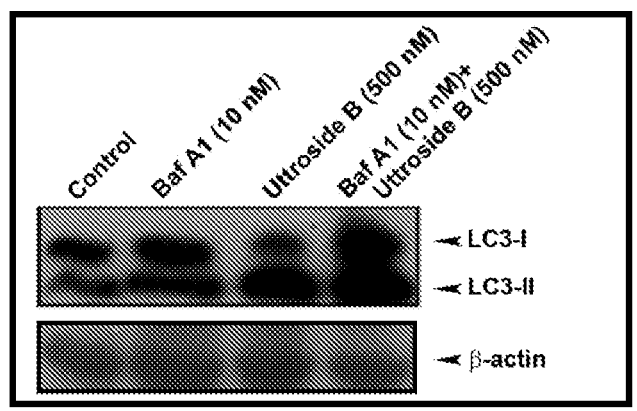
FIG. 27 shows that Uttroside B is an autophagy inducer in HepG2 cells. Cells were treated with Uttroside B (500 nM) and/or Bafilomycin Al (10 nM) for 24 h on the endogenous conversion of LC3I to LC3II and the whole cell lysate was resolved on a 15% gel and immunoblotted against, LC3 antibody.

FIG. 27 shows that Uttroside B is an autophagy inducer in HepG2 cells. Cells were treated with Uttroside B (500 nM) and/or Bafilomycin Al (10 nM) for 24 h on the endogenous conversion of LC3I to LC3II and the whole cell lysate was resolved on a 15% gel and immunoblotted against, LC3 antibody. This concentration of Bafilomycin, when co-treated with Uttroside B caused a surplus accumulation of LC3II in HepG2 cells compared to the cells treated with either Bafilomycin or Uttroside B alone. If Uttroside B is an autophagy blocker there should not be any further enhancement of expression of LC3II as autophagy is already blocked. This surplus accumulation of LC3II induced by Uttroside B in the presence of Bafilomycin Al demonstrates an enhanced autophagic flux due to Uttroside B treatment, which strongly proves that Uttroside B is an autophagy inducer.

Figure 28:
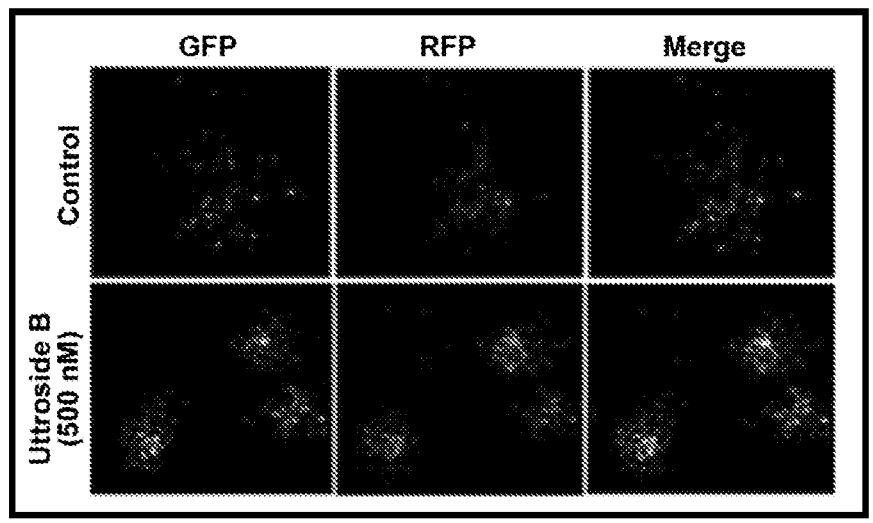
FIG. 28 shows the autophagy flux assay using PtfLC3 reporter protein.
Figure 29:
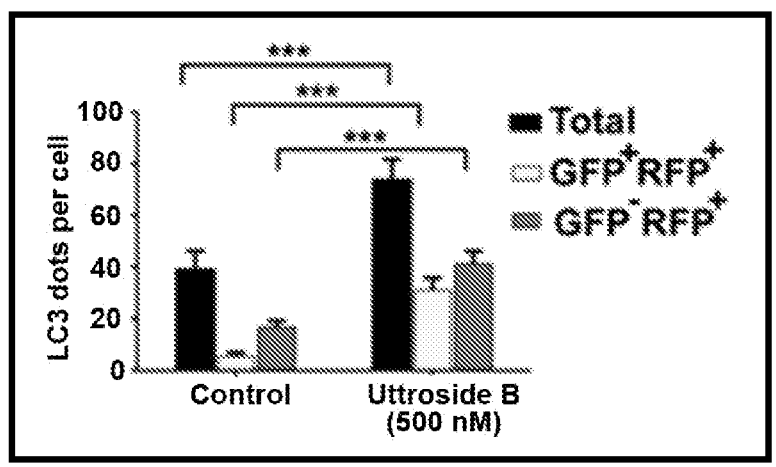
FIG. 29 is a bar diagram showing the quantitative analysis of autophagy induced by Uttroside B in HepG2 cells.

Quantitative analysis of autophagy flux using tandem GFP-RFP LC3 reporter protein. FIG. 28 shows the autophagy flux assay using PtfLC3 reporter protein. HepG2 cells were transiently transfected with PtfLC3 reporter plasmid encoding GFP-RFP-LC3, cultured in complete medium for 24 h and treated with Uttroside B (500 nM) for 24 h. Representative images of cells showing GFP-RFP-LC3 punctae are photographed under confocal microscopy. Scale bar, 20 μm. FIG. 29 is a bar diagram showing the quantitative analysis of autophagy induced by Uttroside B in HepG2 cells. HepG2 cells were transfected transiently with plasmid encoding GFP-RFP-LC3 as described previously and the punctae observed were counted and plotted as a histogram. The next attempt was to verify and quantitate the autophagic flux induced by Uttroside B using a tandem GFP-RFP LC3 reporter protein. GFP and RFP will florescence depending upon the pH condition of the cell. If the pH of the autophagosomes is above 5, both GFP and RFP will fluoresce and the autophagosome will fluoresce as yellow due to the merging of green and red. If the pH is below 5 i.e. acidic due to the fusion of autophagosome and lysosome, the GFP will be quenched and only the RFP will fluoresce and the cell will appear as red punctae[32,35,39]. HepG2 cells were transfected with the reporter plasmid ptfLC3 which contain the tandem repeats of GPF-RFP fused with LC3. The plasmid gets integrated into autophagosomes in the cells, which fluoresce as punctae. When the transfected cells were treated with Uttroside B, there was an increase in amount of yellow puncta and red puncta indicating that there occurs the formation of autophagosome and its conversion into autophagolysosome i.e. the autophagy flux. In other words, Uttroside B-treated cells shows an increase in GFP+RFP+ (autophagosomes) along with GFP−RFP+ (autophagolysosomes) which implies an enhancement of autophagosomes and its progression to autophagolysosomes and an increase in autophagy, which have been quantitated by counting the puncti, plotting it graphically. All these evidences illustrate that Uttroside Bis an efficient autophagy inducer.

Figure 30:
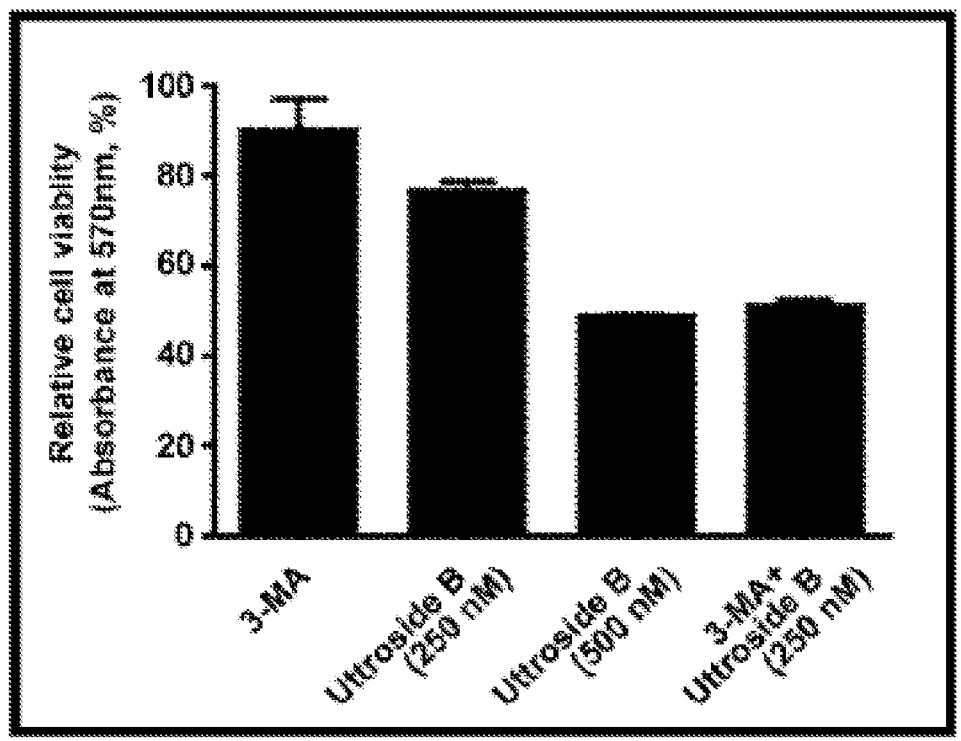
FIG. 30 shows the bar diagram indicating the inhibition of autophagy by 3-MA significantly enhanced Uttroside B-induced cytotoxicity.
Figure 31:
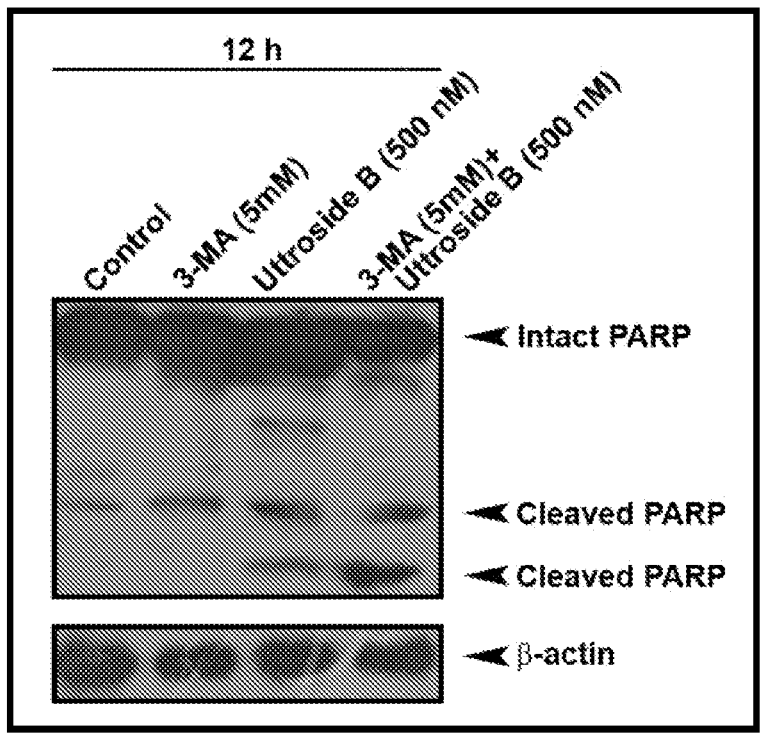
FIG. 31 shows the Western blot indicating that Uttroside B-induced cleavage of PARP in HepG2 cells is enhanced by 3-MA, an autophagy inhibitor.
Figure 32:
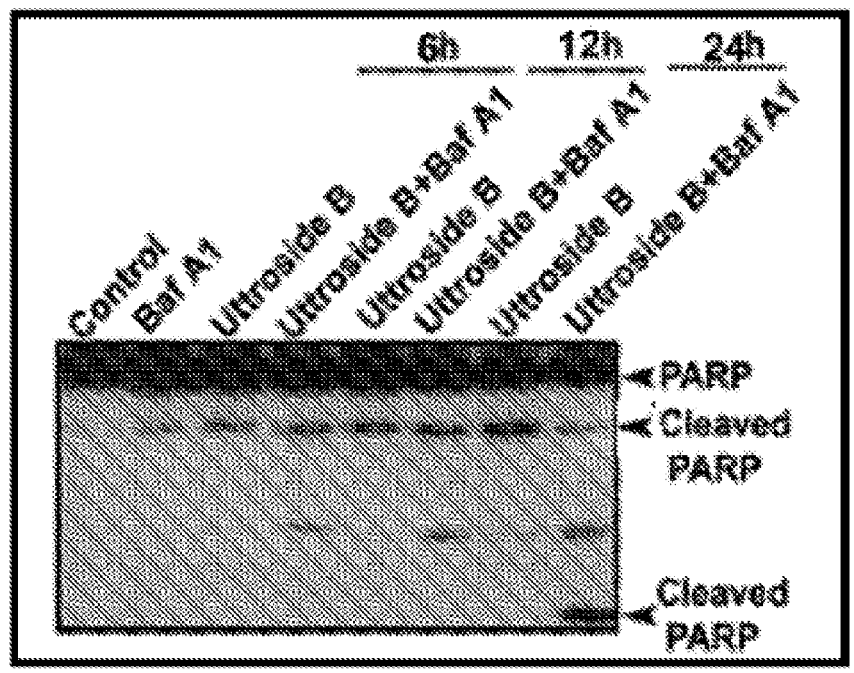
FIG. 32 shows the Western blot indicating that Uttroside B induced cleavage of PARP in HepG2 cells is enhanced by Bafilomycin Al, an autophagy inhibitor.
Figure 33:
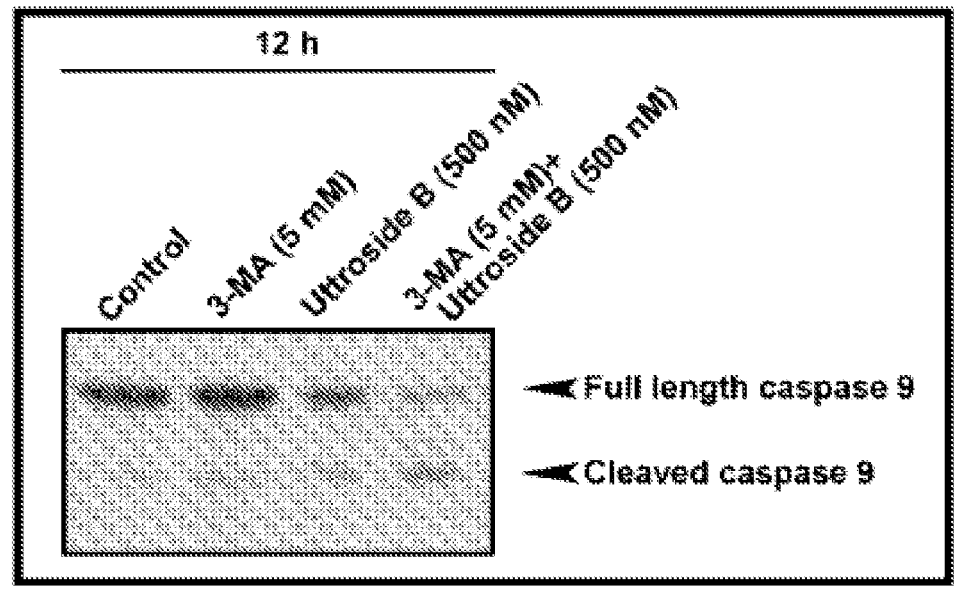
FIG. 33 shows the Western blot indicating that Uttroside B induced cleavage of caspase 9 activation in HepG2 cells is enhanced by 3-MA, an autophagy inhibitor.
Figure 34:
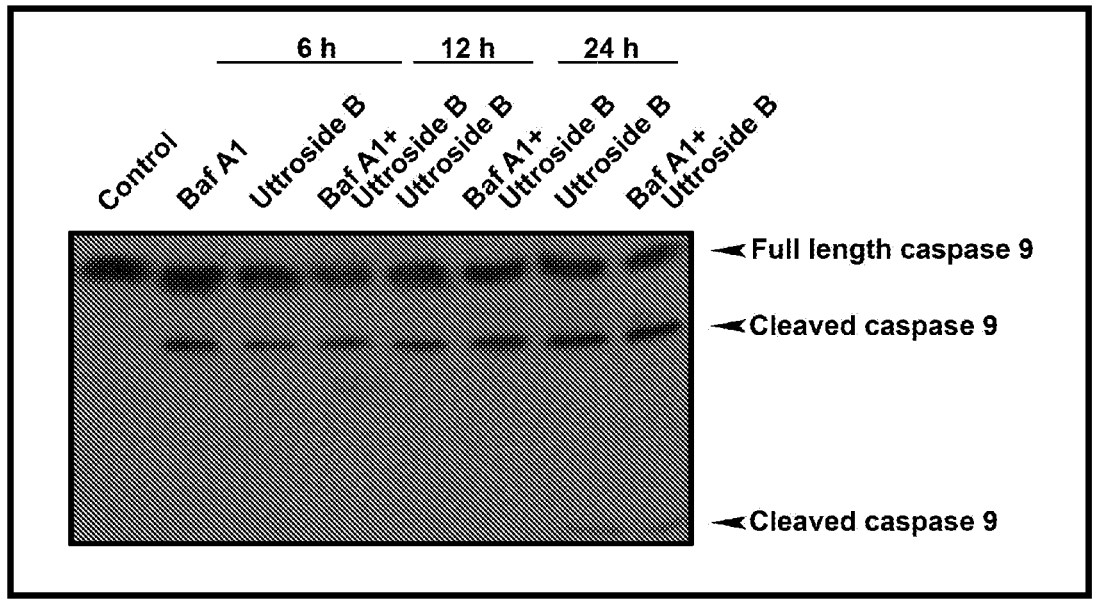
FIG. 34 shows the Western blot indicating that Uttroside B induced caspase 9 activation in HepG2 cells is enhanced by Bafilomycin Al, an autophagy inhibitor.
Figure 35:
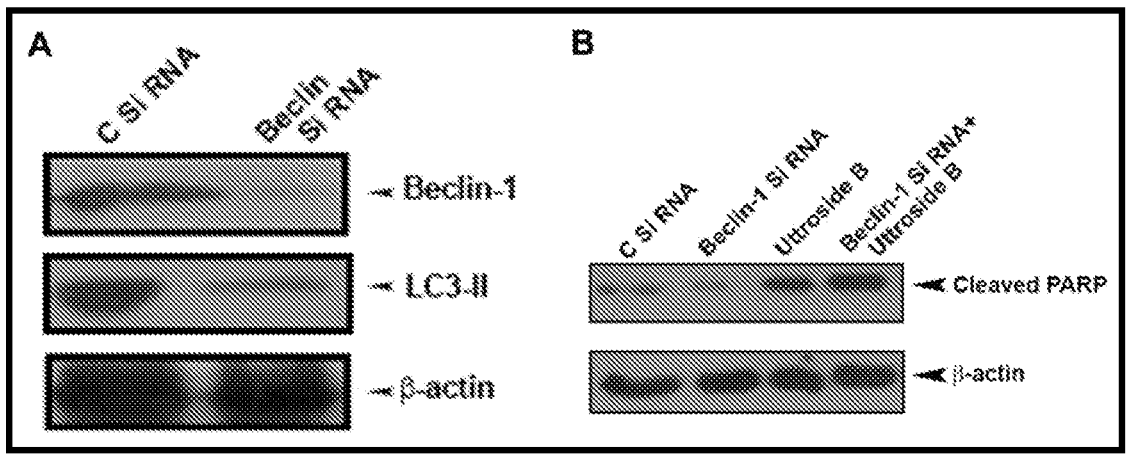
FIG. 35 shows the Western blot indicating that Uttroside B-induced PARP cleavage in HepG2 cells is enhanced by genetic silencing of Beclin-1.

Inhibition of autophagy enhances the cytotoxicity and apoptosis induced by Uttroside B in HepG2. Autophagy and apoptosis often occur in the same cell, mostly in a sequence in which autophagy precedes apoptosis. This is because stress often stimulates an autophagic response, especially if the level of stress is not lethal.[40] In preclinical models, inhibition of pro-survival autophagy by genetic or pharmacological means was shown to kill tumor cells and trigger apoptotic cell death.[41, 42] The role of Uttroside B-induced autophagy in regulating the apoptotic program of HepG2 was analyzed using two pharmacological inhibitors of autophagy, namely 3-MA and Bafilomycin Al.[32] For evaluating this aspect, HepG2 cells were exposed to Uttroside B with or without the inhibitors and the enhancement in cytotoxicity was assessed by MTT assay and extent of apoptosis was analyzed by monitoring cleavage of PARP and caspase 9. 3-MA is a class 3 PI3K kinase inhibitor which blocks the early stage of autophagy and Bafilomycin Al is a late stage inhibitor of autophagy, which blocks the fusion of autophagosome and lysosome. In FIG. 30 the inhibition of autophagy by 3-MA significantly enhanced Uttroside B-induced cytotoxicity, HepG2 cells were treated with Uttroside B with or without 3 MA (1 mM) as indicated, incubated for 72 h and the cell viability was assessed by MTT assay and FIG. 31 (Uttroside B-induced cleavage of PARP in HepG2 cells is enhanced by 3-MA, an autophagy inhibitor. HepG2 cells were treated with Uttroside B and/or 3-MA for 12 h and the whole cell lysate was resolved on a 10% gel and immunoblotted against PARP antibody and detected by ECL) & FIG. 34 (Uttroside B induced cleavage of PARP in HepG2 cells is enhanced by Bafilomycin Al, an autophagy inhibitor. HepG2 cells were treated with Uttroside B and/or Bafilomycin-Al for different time periods and the whole cell lysate was resolved on a 10% gel and immunoblotted against PARP antibody and detected by ECL) pretreatment with both the inhibitors, 3-MA and Bafilomycin-Al enhanced UttrosideB-induced cleavage of PARP and in FIG. 32 (Uttroside B induced cleavage of PARP activation in HepG2 cells is enhanced by 3-MA, an autophagy inhibitor. HepG2 cells were treated with Uttroside B and/or 3-MA for 12 h and the whole cell lysate was resolved on a 15% gel and immunoblotted against PARP antibody and detected by ECL) & FIG. 33 (Uttroside B induced caspase 9 activation in HepG2 cells is enhanced by Bafilomycin Al, an autophagy inhibitor. HepG2 cells were treated with Uttroside B and/or Bafilomycin Al for different time periods and the whole cell lysate was resolved on a 15% gel and immunoblotted against PARP antibody and detected by ECL) caspase 9. The results clearly indicate that inhibition of autophagy by 3-MA and Bafilomycin-Al enhances the potential of Uttroside B inducing cytotoxicity and apoptosis in HepG2 cells. This observation was confirmed by genetic inhibition of autophagy by silencing beclin-1. In many cases, the role of autophagy is identified through studies of an autophagy-related protein, Atg6/Beclin 1. This protein is part of a lipid kinase complex and recent studies suggest that it plays a central role in coordinating the cytoprotective function of autophagy and in opposing the cellular death process of apoptosis.[42] FIG. 35A (Uttroside B-induced PARP cleavage in HepG2 cells is enhanced by genetic silencing of Beclin-1. (a) HepG2 cells were transiently transfected with Beclin siRNA and autophagy inhibition was confirmed by immunoblotting) autophagic inhibition in beclin-1 inhibited cells were confirmed by LC3 immunoblotting analysis. In FIG. 35B (Beclin-1 silenced HepG2 cells were treated with or without Uttroside B for 24 h and the whole cell lysate was resolved on a 10% gel and immunoblotted against PARP antibody) when beclin-1 expression was inhibited using siRNA, a strong enhancement was observed in Uttroside B-induced apoptosis as evidenced by the increase in the expression of cleaved PARP. This experiment confirms that the anticancer efficacy of Uttroside B can be further enhanced when an inhibitor of autophagy is used along with it.

Besides apoptosis, Uttroside B also induces vacuolated structures, characteristics of autophagy and induces activation of autophagy markers such as LC3 II, Beclin 1, Atg7, Atg5, Atg12 and Atg3 in liver cancer cells, Hepg2 and Hep3B. The increase in autophagy flux in HepG2 cells treated with Uttroside B was confirmed using Bafilomycin Al and quantitated by RFP-GFP-LC3 tagged protein assay which illustrates Uttroside is an autophagy inducer. Uttroside down regulates the mTOR and its downstream targets p-70S6 kinase and 4E-BP-1. The pharmacological (using Bafilomycin Al) and genetic (using Beclin-1 si-RNA) blockage of autophagy enhance Uttroside B-induced apoptosis, which illustrate that autophagy is the negative regulator of Uttroside B-mediated apoptosis.

Liver cancer cells exhibited maximum sensitivity to Uttroside B-mediated cytotoxicity, while not affecting the normal immortalized liver cells. Uttroside B is pharmacologically safe as accessed by liver function tests and histopathological analysis.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to deteimine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue study in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Vincken, J.-P.; Heng, L.; de Groot, A.; Gruppen, H. Phytochemistry. 2007, 68, 275-297.
2. Man, S.; Gao, W.; Zhang. Y.; Huang, L.; Liu, C. Fitoterapia. 2010, 81, 703-714.
3. Podolak, I.; Galanty, A.; Sobolewska, D. Phytochem. Rev. 2010, 9, 425-474.
4. Nohara, T.; Ikeda, T.; Fujiwara, Y.; Matsushita, S.; Noguchi, E.; Yoshimitsu, H.; Ono, M. J. Nat. Med. 2007, 61, 1-13.
5. Milner, S. E.; Brunton, N. P.; Jones, P. W.; O'Brien, N. M.; Collins, S. G.; Maguire, A. R. J. Agric. Food. Chem. 2011, 59, 3454-3484.
6. Jain, R.; Sharma, A.; Gupta, S.; Sarethy, I. P.; Gabrani, R. J. Clin. Ther. 2011, 16, 78-85.

7. Hu, K.; Kobayashi, H.; Dong, A.; Jing, Y.; Iwasaki, S.; Yao, X. Planta Med. 1999, 65, 35-38.
8. Ikeda, T.; Tsumagari, H.; Nohara, T. Chem. Pharm. Bull. 2000, 48, 1062-1064.
9. Zhou, X.; He, X.; Wang, G.; Gao, H.; Zhou, G.; Ye, W.; Yao, X. J. Nat. Prod. 2006, 69, 1158-1163.
10. Sharma, S. C.; Chand, R.; Sati, O. P.; Sharma, A. K. Phytochemistry. 1983, 22, 1241-1244.
11. Wu, K.-L.; Kang, L.-P.; Xiong, C.-Q.; Zhao, Y.; Yu, H.-S.; Zhang, J.; Ma, B-P. J. Tianjin Univ. Trad. Chin. Med. 2012, 31, 225-228.
12. Jin, J.-M.; Zhang, Y.-J.; Yang, C.-R. J. Nat. Prod. 2004, 67, 5-9.
13. Ikeda, T.; Tsumagari, H.; Honbu, T.; Nohara, T. Chem. Pharm. Bull. 2003, 26, 1198-1201.
14. Perrone, A.; Plaza, A.; Bloise, E.; Nigro, P.; Hamed, A. I.; Belisario, M. A.; Pizza, C.; Piacente, S. J. Nat. Prod. 2005, 68, 1549-1553.
15. Pittelkow, M. R.; Scott, R. E. Mayo Clin Proc. 1986, 61, 771-777.
16. Franken, N. A. P.; Rodermond, H. M.; Stap, J.; Haveman, J.; van Bree, C. Nat. Protoc.2006, 1, 2315-2319.
17. Antony, J.; Saikia, M.; Vinod, V.; Nath, L. R.; Katiki, M. R.; Murty, M. S.; Paul, A.; Shabna, A.; Chandran, H.; Joseph, S. M.; Nishanth, K. S.; Panakkal, E. J.; Sriramya, I.; Sridivya, I.; Ran, S.; Sankar, S.; Rajan, E.; Anto, R. J. Sci. Rep. 2015, 5, 11107.
18. da Rocha, A. B.; Lopes, R. M.; Schwartsmann, G. Curr. Opin. Pharmacol. 2001, 1, 364-369.
19. Itokawa, H.; Wang, X.; Lee K. H. Brunner-Routledge Psychology Press, Taylor & Francis Group, Boca Raton. 2005, 4, 47.
20. Laladhas, K. P.; Cheriyan, V. T.; Puliappadamba, V. T.; Bava, S. V.; Unnithan, R. G.; Vijayammal, P. L.; Anto, R. J. J. Cell. Mol. Med. 2011, 14, 636-646.
21. Raju, J.; Mehta, R.; Nutr. Cancer. 2009, 61, 27-35.
22. Wang, G.; Huang, W.; He, H.; Fu, X.; Wang, J.; Zou, K.; Chen, J. Int J Mol Med. 2013, 31, 219-224.
23. Amin, A. R.; Kucuk, O.; Khuri, F. R.; Shin, D. M. J. Clin. Oncol. 2009, 27, 2712-2725.
24. Mclet, A.; Song, K.; Bucur, O.; Jagani, Z.; Grassian, A. R.; Khosravi-Far, R. Adv. Exp. Med. Biol. 2008, 615, 47-79.
25. Trouillas, P.; Corbiere, C.; Liagre, B.; Duroux, J. L.; Beneytout, J. L. Bioorg. Med. Chem. 2005, 13, 1141-1149.
26. Sun, B. Karin, M. Oncogene. 2008, 27, 6228-6244.
27. Wu, X.; Li, Y. InTech, Prof. Alexander Juliano (Ed.), 2012, ISBN: 978-953-51-0036-2.
28. Guertin, D. A.; Sabatini, D. M. Cancer Cell, 2007, 12, 9-22.
29. Wang, C.; Wang, X.; Su, Z.; Fei, H.; Liu, X.; Pan, Q. Oncol. Rep. 2015, 34, 1708-1716.
30. Matter, M. S.; Decaens, T.; Andersen, J. B.; Thorgeirsson, S. S. J. Hepatol. 2014, 60, 855-865.
31. Wang, C.; Cigliano, A.; Delogu, S.; Armbruster, J.; Dombrowski, F.; Evert, M.; Chen, X.; Diego F. Cell. Cycle. 2013, 12, 1999-2010.
32. Klionsky D J, Abdalla F C, Abeliovich H, Abraham R T, Acevedo-Arozena A, Adeli K et al (2012). Guidelines for the use and interpretation of assays for monitoring autophagy. Autophagy 8: 445-544.
33. Nyfeler B, Bergman P, Wilson C J, Murphy L O (2012). Quantitative visualization of autophagy induction by mTOR inhibitors. Methods MolBiol 821: 239-250.
34. Mizushima N, Yoshimori T (2007). How to interpret LC3 immunoblotting. Autophagy 3: 542-545.
35. Mizushima N, Yamamoto A, Matsui M, Yoshimori T, Ohsumi Y (2004). In vivo analysis of autophagy in response to nutrient starvation using transgenic mice expressing a fluorescent autophagosome marker. Mol Biol Cell 15: 1101-1111.
36. Meijer A J, Codogno P (2004). Regulation and role of autophagy in mammalian cells. Int J Biochem Cell Biol 36: 2445-2462.
37. Mizushima N, Yoshimori T, Levine B (2010). Methods in mammalian autophagy research. Cell 140: 313-326.
38. Yu R, Zhang Z Q, Wang B, Jiang H X, Cheng L, Shen L M (2014). Berberine-induced apoptotic and autophagic death of HepG2 cells requires AMPK activation. Cancer Cell Int 14:49.
39. Tanida I, Tanida-Miyake E, Ueno T, Kominami E (2001). The human homolog of *Saccharomyces cerevisiae* Apg7p is a Protein-activating enzyme for multiple substrates including human Apg12p, GATE-16, GAB ARAP, and MAP-LC3. J Biol Chem 276: 1701-1706.
40. Marino G, Niso-Santano M, Baehrecke E H, Kroemer G (2014). Self-consumption: the interplay of autophagy and apoptosis. Nat Rev Mol Cell Biol 15: 81-94.
41. White E, DiPaola R S (2009). The double-edged sword of autophagy modulation in cancer. Clin Cancer Res 15: 5308-5316.
42. Yang Z J, Chee C E, Huang S, Sinicrope F (2011). Autophagy modulation for cancer therapy. Cancer BiolTher 11: 169-176.

The invention claimed is:

1. A method of treating a patient diagnosed with liver cancer comprising administering to the patient a pharmaceutical composition containing a pharmaceutically effective amount of Uttroside B having the formula:

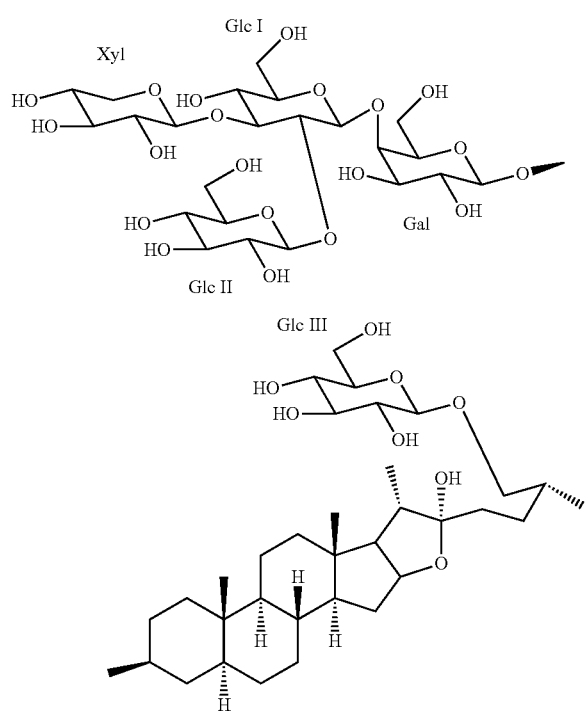

7. The method of claim 1, wherein the Uttroside B has a concentration range of about 10 mg per kg body weight of the patient.

8. The method of claim 1, wherein the provided pharmaceutically effective amount of Uttroside B is provided in an amount sufficient to cause apoptosis, autophagy, down-regulation of MAPK pathways, down-regulation of mTOR pathways or a combination thereof in one or more liver cancer cells.

9. The method of claim 1, wherein the Uttroside B has an in vitro concentration of between 0.66 µM and 2 mM.

10. The method of claim 1, wherein the in vitro concentration of Uttroside B is between or between 0.132 and 1.05 mM.

11. A method of treating a patient with a condition selected from one of Fibrolamellar carcinoma, Cholangiocarcinoma, Angiosarcoma, and Hepatoblastoma, the method comprising administering to the patient a pharmaceutical composition containing a pharmaceutically effective amount of Uttroside B having the formula:

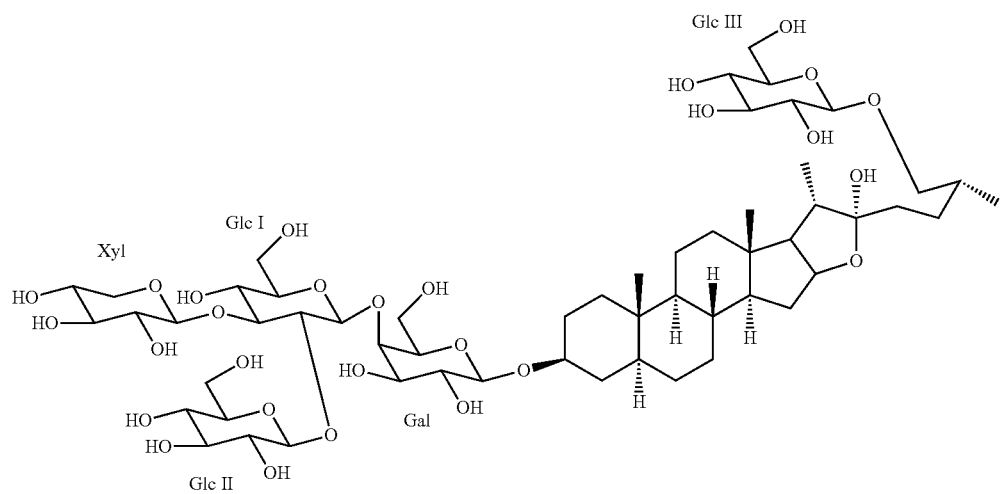

so as to maintain an in vivo concentration of Uttroside B between 0.066 and 1.32 nM within the subject and at least a second therapeutic agent.

2. The method of claim 1, wherein the second therapeutic agent is Chloroquine.

3. The method of claim 1, wherein the second therapeutic agent is a proline oligomer or free proline.

4. The method of claim 1, wherein the second therapeutic agent is glutathione or oligomers of glutathione.

5. The method of claim 1, wherein the second therapeutic agent is sorafenib.

6. The method of claim 1, wherein the Uttroside B has a concentration range of between 0.05 and 150 mg per kg body weight of the patient.

so as to maintain an in vivo concentration of Uttroside B between 0.066 and 1.32 nM within the subject wherein the pharmaceutically effective amount of Uttroside B is sufficient to treat the condition.

12. A method of impeding the growth of a liver cancer tumor comprising administering to a patient with a liver cancer tumor a pharmaceutical composition containing a pharmaceutically effective amount of Uttroside B having the formula:

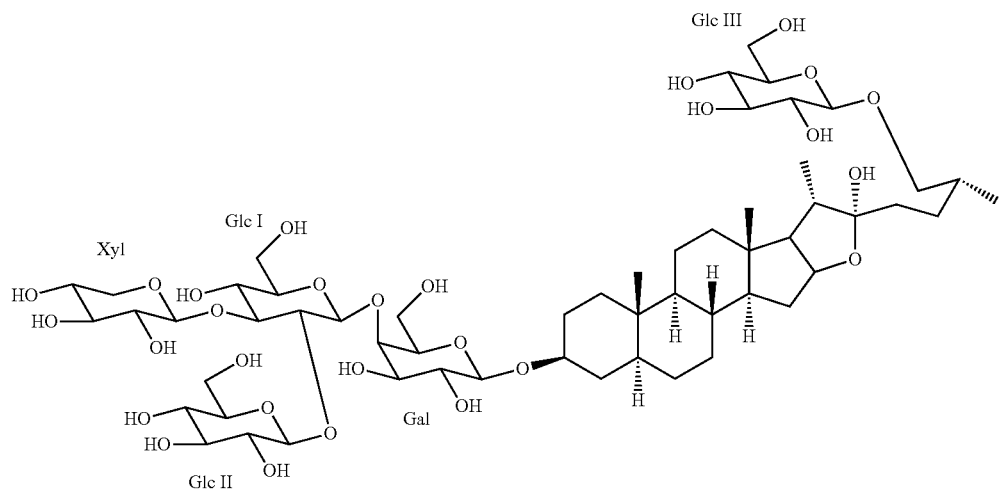

so as to maintain an in vivo concentration of Uttroside B between 0.066 and 1.32 nM within the subject and at least a second therapeutic agent wherein the pharmaceutically effective amount of Uttroside B is sufficient to impede the growth of a liver cancer tumor.

13. The method of claim 12, wherein the second therapeutic agent includes proline.

14. The method of claim 12, wherein the second therapeutic agent includes Chloroquine.

15. The method of claim 12, wherein the second therapeutic agent includes a proline oligomer or free proline.

16. The method of claim 12, wherein the second therapeutic agent includes glutathione or oligomers of glutathione.

17. The method of claim 12 wherein the second therapeutic agent includes sorafenib.

\* \* \* \* \*